(12) United States Patent
Milne et al.

(10) Patent No.: US 9,029,548 B2
(45) Date of Patent: May 12, 2015

(54) FATTY ACID LENALIDOMIDE DERIVATIVES AND THEIR USES

(75) Inventors: Jill C. Milne, Brookline, MA (US); Michael R. Jirousek, Cambridge, MA (US); Jean E. Bemis, Arlington, MA (US); Chi B. Vu, Arlington, MA (US); Amal Ting, Newton, MA (US)

(73) Assignee: Catabasis Pharmaceuticals, Inc., Cambridge, MA (US)

( * ) Notice: Subject to any disclaimer, the term of this patent is extended or adjusted under 35 U.S.C. 154(b) by 266 days.

(21) Appl. No.: 13/464,435

(22) Filed: May 4, 2012

(65) Prior Publication Data

US 2012/0283292 A1 Nov. 8, 2012

Related U.S. Application Data

(60) Provisional application No. 61/483,367, filed on May 6, 2011.

(51) Int. Cl.
*C07D 401/00* (2006.01)
*A61K 31/445* (2006.01)
*C07D 401/04* (2006.01)
*A61K 47/48* (2006.01)

(52) U.S. Cl.
CPC ........ *C07D 401/04* (2013.01); *A61K 47/48038* (2013.01)

(58) Field of Classification Search
CPC ...................................................... C07D 401/00
USPC .......................................... 546/201; 514/323
See application file for complete search history.

(56) References Cited

U.S. PATENT DOCUMENTS 7,091,353 B2 * 8/2006 Robarge et al. ............... 546/200
2011/0223611 A1 * 9/2011 Salamone et al. ............. 435/7.1

\* cited by examiner

*Primary Examiner* — John Mabry
(74) *Attorney, Agent, or Firm* — Goodwin Procter LLP

(57) ABSTRACT

The invention relates to fatty acid lenalidomide derivatives; compositions comprising an effective amount of a fatty acid lenalidomide derivative; and methods for treating or preventing a metabolic disease comprising the administration of an effective amount of a fatty acid lenalidomide derivative.

6 Claims, No Drawings

FATTY ACID LENALIDOMIDE DERIVATIVES AND THEIR USES

CROSS-REFERENCE TO RELATED APPLICATIONS

This application claims priority to and the benefit of U.S. Provisional Application Ser. No. 61/483,367, filed May 6, 2011, the disclosure of which is hereby incorporated by reference in its entirety.

FIELD OF THE INVENTION

The invention relates to fatty acid lenalidomide derivatives; compositions comprising an effective amount of a fatty acid lenalidomide derivative; and methods for treating or preventing a metabolic disease comprising the administration of an effective amount of a fatty acid lenalidomide de rivative. All patents, patent applications, and publications cited herein are hereby incorporated by reference in their entireties.

BACKGROUND OF THE INVENTION

Oily cold water fish, such as salmon, trout, herring, and tuna are the source of dietary marine omega-3 fatty acids, with eicosapentaenoic acid (EPA) and docosahexaenoic acid (DHA) being the key marine derived omega-3 fatty acids. Omega-3 fatty acids have previously been shown to improve insulin sensitivity and glucose tolerance in normoglycemic men and in obese individuals. Omega-3 fatty acids have also been shown to improve insulin resistance in obese and non-obese patients with an inflammatory phenotype. Lipid, glucose, and insulin metabolism have been shown to improve in overweight hypertensive subjects through treatment with omega-3 fatty acids. Omega-3 fatty acids (EPA/DHA) have also been shown to decrease triglycerides and to reduce the risk for sudden death caused by cardiac arrhythmias in addition to improve mortality in patients at risk of a cardiovascular event. Omega-3 fatty acids have also been taken as dietary supplements part of therapy used to treat dyslipidemia, and anti-inflammatory properties. A higher intake of omega-3 fatty acids lower levels of circulating TNF-α and IL-6, two of the cytokines that are markedly increased during inflammation processes (Chapkin et al, *Prostaglandins, Leukot Essent Fatty Acids* 2009, 81, p. 187-191; Duda et al, *Cardiovasc Res* 2009, 84, p. 33-41). In addition, a higher intake of omega-3 fatty acids has also been shown to increase levels of the well-characterized anti-inflammatory cytokine IL-10 (Bradley et al, *Obesity (Silver Spring)* 2008, 16, p. 938-944). More recently, there is additional evidence that omega-3 fatty acids could play a significant role in oncology (Anderson et al, *Lipids in Health and Disease* 2009, 8, p. 33; Bougnoux et al, *Progress in Lipid Research* 2010, 49, p. 76-86; Erickson et al, *Prostaglandins, Leukotrienes and Essential Fatty Acids* 2010, 82, p. 237-241). In a study using the xenograft model in nude mice, treatment with omega-3 fatty acids, such as DHA and EPA, resulted in breast tumor regression. Here, treatment with DHA/EPA appeared to increase the level of PTEN protein and attenuate the PI 3 kinase and Akt kinase activity as well as the expression of the anti-apoptotic proteins Bcl-2 and Bcl-XL in the breast tumors (Ghosh-Choudhury, T. et al. *Breast Cancer Res. Treat.* 2009, 118 (1), 213-228). Additional evidence supporting the use of omega-3 fatty acids in oncology also appeared in a recent study by Lim et al. showing that DHA/EPA could inhibit hepatocellular carcinoma cell growth, presumably by blocking β-catenin and cyclooxygenase-2 (Lim, K. et al. *Mol. Cancer Ther.* 2009, 8 (11), 3046-3055).

Both DHA and EPA are characterized as long chain fatty acids (aliphatic portion between 12-22 carbons). Medium chain fatty acids are characterized as those having the aliphatic portion between 6-12 carbons. Lipoic acid is a medium chain fatty acid found naturally in the body. It plays many important roles such as free radical scavenger, chelator to heavy metals and signal transduction mediator in various inflammatory and metabolic pathways, including the NF-κB pathway (Shay, K. P. et al. *Biochim. Biophys. Acta* 2009, 1790, 1149-1160). Lipoic acid has been found to be useful in a number of chronic diseases that are associated with oxidative stress (for a review see Smith, A. R. et al *Curr. Med. Chem.* 2004, 11, p. 1135-46). Lipoic acid has now been evaluated in the clinic for the treatment of diabetes (Morcos, M. et al *Diabetes Res. Clin. Pract.* 2001, 52, p. 175-183) and diabetic neuropathy (Mijnhout, G. S. et al *Neth. J. Med.* 2010, 110, p. 158-162). Lipoic acid has also been found to be potentially useful in treating cardiovascular diseases (Ghibu, S. et al, *J. Cardiovasc. Pharmacol.* 2009, 54, p. 391-8), Alzheimer's disease (Maczurek, A. et al, *Adv. Drug Deliv. Rev.* 2008, 60, p. 1463-70) and multiple sclerosis (Yadav, V. *Multiple Sclerosis* 2005, 11, p. 159-65; Salinthone, S. et al, *Endocr. Metab. Immune Disord. Drug Targets* 2008, 8, p. 132-42).

Lenalidomide is an anti-cancer agent that has been approved by the FDA for the treatment of multiple myeloma in combination with dexamethasone. Lenalidomide has also been approved for use in patients with transfusion-dependent anemia due to Low or Intermediate-1-risk myelodysplastic syndromes (MDS) associated with a deletion 5q cytogenetic abnormality with or without additional cytogenetic abnormalities. Lenalidomide belongs to the Immunomodulatory imide Drugs (IMiDs) class of compounds and is essentially an analogue of thalidomide (Rajkumar et al, *Blood* 2005, 106, p. 4050-4053; Dredge et al, *British J. Cancer* 2002, 87, p. 1166-1172). In terms of mechanism of action, lenalidomide can act as immunomodulator agent because of its ability to inhibit IL-1β or TNF-α-induced activation of IκK, which in turn prevents dissociation of IκBα from NF-κB, precluding its nuclear translocation and induction of various genes that are responsible for metastasis, angiogenesis, cellular proliferation, inflammation and protection from apoptosis (Aragon-Ching et al, *Recent Pat Anticancer Drug Discov.* 2007, 2, p. 167-174). Pomalidomide is another derivative of lenalidomide that has also been shown to have interesting anti-cancer activity (Tefferi et al, *J. Clin. Oncology* 2009, 27, p. 4563-4569).

Because of the ability of lenalidomide and omega-3 fatty acid to act on the NF-κB axis, a synergistic activity would provide a great benefit in treating multiple myeloma, myelodysplastic syndromes (MDS) or other metabolic diseases.

SUMMARY OF THE INVENTION

The invention is based in part on the discovery of fatty acid lenalidomide derivatives and their demonstrated effects in achieving improved treatment that cannot be achieved by administering lenalidomide or fatty acids alone or in combination. The fatty acid lenalidomide derivatives are designed to be stable in the plasma. In target tissues, the individual components (i.e. fatty acid, lenalidomide) are then released by the action of various intracellular enzymes. These novel compounds are useful in the treatment or prevention of multiple myeloma, myelodysplastic syndromes (MDS) or other metabolic diseases including including diabetic nephropathy, chronic kidney disease (CKD), atherosclerosis, dyslipidemia, coronary heart disease, hypercholesterimia, Type 2 diabetes, elevated cholesterol, metabolic syndrome and cardiovascular disease. In addition, they are useful in the treatment of autoimmune diseases such as rheumatoid arthritis, cystic fibrosis, inflammatory bowel diseases (including colitis and Crohn's disease).

Accordingly in one aspect, a molecular conjugate is described which comprises an lenalidomide covalently linked to a fatty acid, wherein the fatty acid is selected from the group consisting of omega-3 fatty acids and fatty acids that are metabolized in vivo to omega-3 fatty acids, and the conjugate is capable of hydrolysis to produce free lenalidomide and free fatty acid.

In another aspect, compounds of the Formula I are described:

Formula I

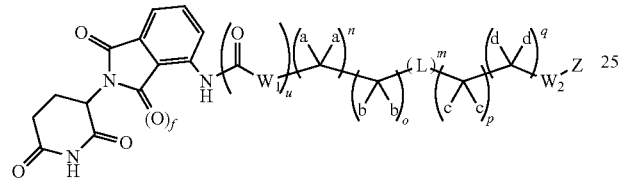

and pharmaceutically acceptable salts, hydrates, solvates, prodrugs, enantiomers and stereoisomers thereof;

$W_1$ and $W_2$ are each independently null, O, S, NH, NR, or $W_1$ and $W_2$ can be taken together can form an imidazolidine or piperazine group;

each a, b, c, and d is independently —H, -D, —$CH_3$, —$OCH_3$, —$OCH_2CH_3$, —C(O)OR, —O—Z, or benzyl, or two of a, b, c, and d can be taken together, along with the single carbon to which they are bound, to form a cycloalkyl or heterocycle;

each n, o, p, and q is independently 0, 1, or 2;

each u is independently 0 or 1;

L is independently null, —O—, —S—, —S(O)—, —S$(O)_2$—, —S—S—, —($C_1$-$C_6$alkyl)-, —($C_3$-$C_6$cycloalkyl)-, a heterocycle, a heteroaryl,

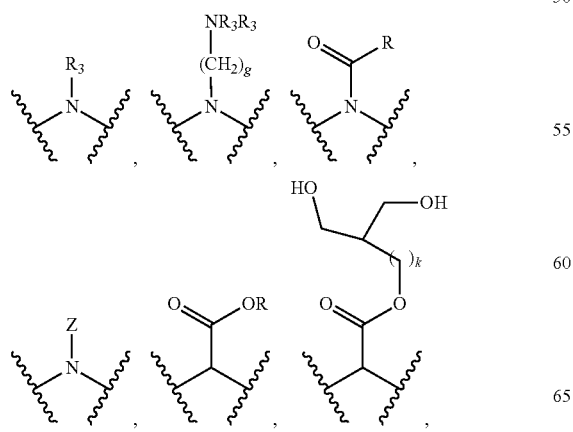

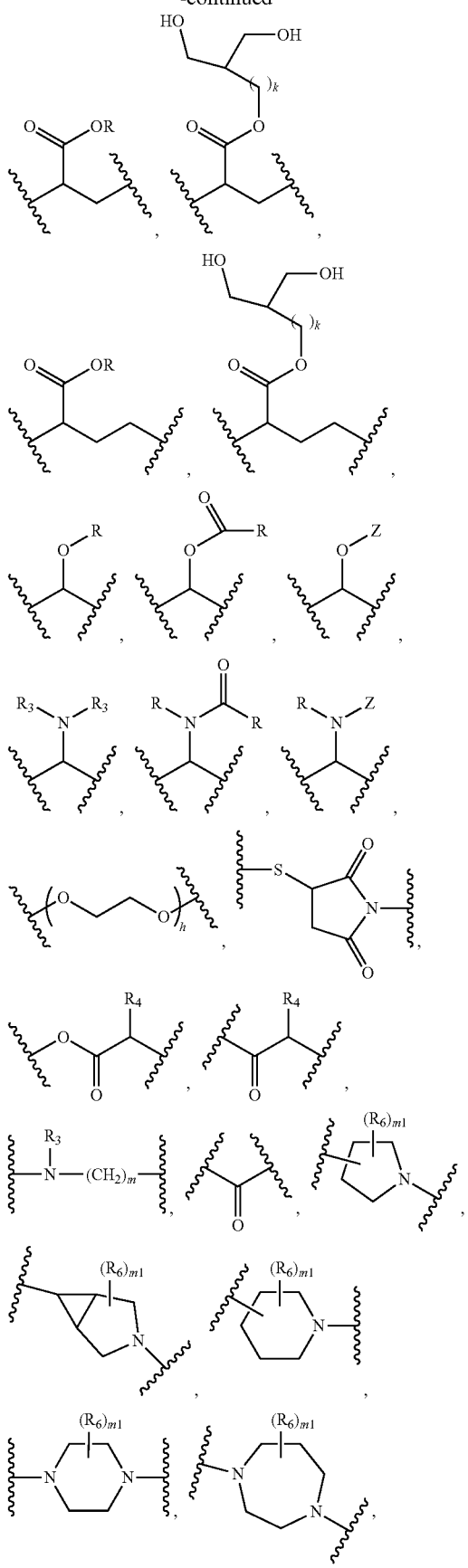

-continued

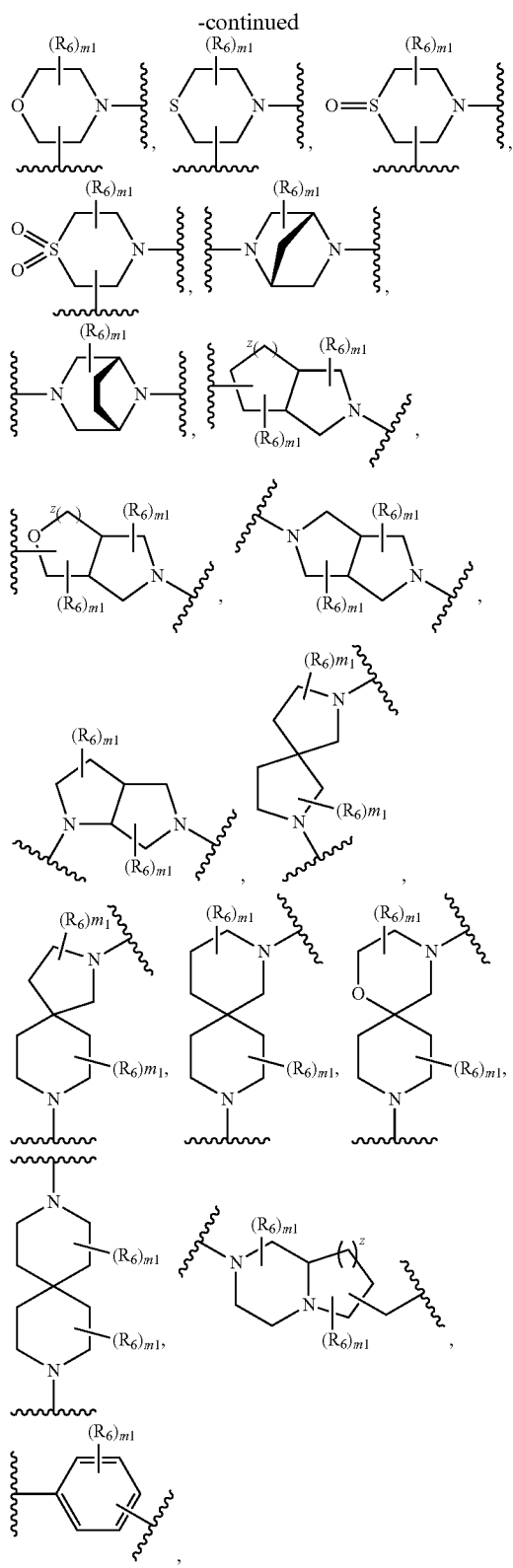

wherein the representation of L is not limited directionally left to right as is depicted, rather either the left side or the right side of L can be bound to the $W_1$ side of the compound of Formula I;

$R_6$ is independently —H, -D, —$C_1$-$C_4$ alkyl, -halogen, cyano, oxo, thiooxo, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;

each f is independently 0 or 1;
each g is independently 2, 3 or 4;
each h is independently 1, 2, 3 or 4;
m is 0, 1, 2, 3, 4 or 5; if m is more than 1, then L can be the same or different;
m1 is 0, 1, 2 or 3;
k is 0, 1, 2, or 3;
z is 1, 2, or 3;
each $R_3$ is independently H or $C_1$-$C_6$ alkyl that can be optionally substituted with either O or N and in $NR_3R_3$, both $R_3$ when taken together with the nitrogen to which they are attached can form a heterocyclic ring such as a pyrrolidine, piperidine, morpholine, piperazine or pyrrole;
each $R_4$ independently e, H or straight or branched $C_1$-$C_{10}$ alkyl which can be optionally substituted with OH, $NH_2$, $CO_2R$, $CONH_2$, phenyl, $C_6H_4OH$, imidazole or arginine;
each e is independently H or any one of the side chains of the naturally occurring amino acids;
each Z is independently —H,

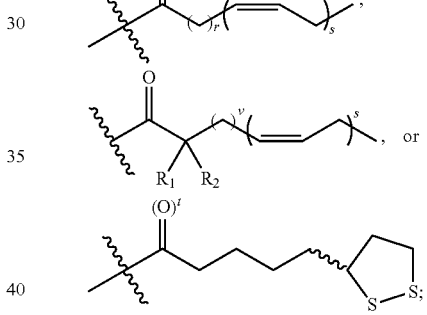

with the proviso that there is at least one of

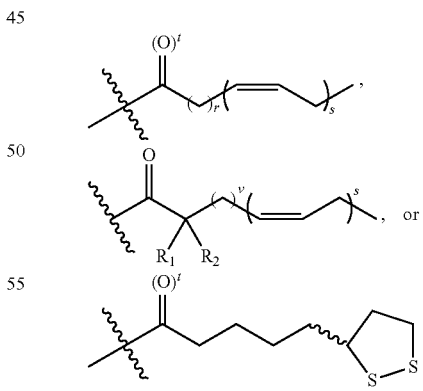

in the compound;
each r is independently 2, 3, or 7;
each s is independently 3, 5, or 6;
each t is independently 0 or 1;
each v is independently 1, 2, or 6;
$R_1$ and $R_2$ are independently —H, -D, —$C_1$-$C_4$ alkyl, -halogen, —OH, —C(O)$C_1$-$C_4$ alkyl, —O-aryl, —O-benzyl, —OC(O)C$_1$-C$_4$ alkyl, —C$_1$-C$_3$ alkene, —C$_1$-C$_3$ alkyne, —C(O)C$_1$-C$_4$ alkyl, —NH$_2$, —NH(C$_1$-C$_3$ alkyl), —N(C$_1$-C$_3$ alkyl)$_2$, —NH(C(O)C$_1$-C$_3$ alkyl), —N(C(O)C$_1$-C$_3$ alkyl)$_2$, —SH, —S(C$_1$-C$_3$ alkyl), —S(O)C$_1$-C$_3$ alkyl, —S(O)$_2$C$_1$-C$_3$ alkyl; and each R is independently —H, —C$_1$-C$_3$ alkyl, or straight or branched C$_1$-C$_4$ alkyl optionally substituted with OH, or halogen;

In another aspect, compounds of the Formula Ia are described:

Formula Ia

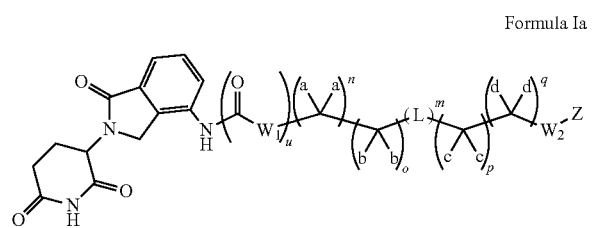

and pharmaceutically acceptable salts, hydrates, solvates, prodrugs, enantiomers and stereoisomers thereof;

W$_1$ and W$_2$ are each independently null, O, S, NH, NR, or W$_1$ and W$_2$ can be taken together can form an imidazolidine or piperazine group;

each a, b, c, and d is independently —H, -D, —CH$_3$, —OCH$_3$, —OCH$_2$CH$_3$, —C(O)OR, —O—Z, or benzyl, or two of a, b, c, and d can be taken together, along with the single carbon to which they are bound, to form a cycloalkyl or heterocycle;

each n, o, p, and q is independently 0, 1, or 2;

each u is independently 0 or 1;

L is independently null, —O—, —S—, —S(O)—, —S(O)$_2$—, —S—S—, —(C$_1$-C$_6$alkyl)-, —(C$_3$-C$_6$cycloalkyl)-, a heterocycle, a heteroaryl,

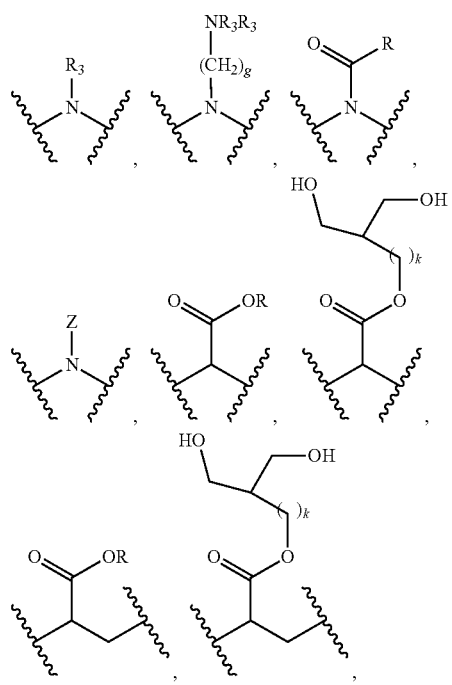

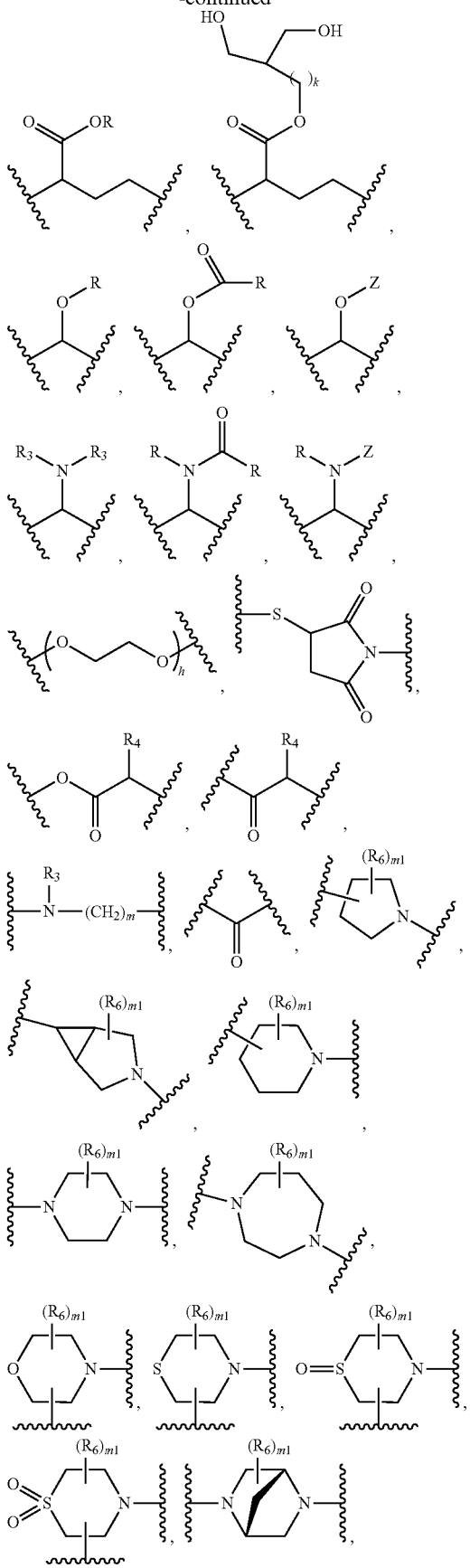

-continued

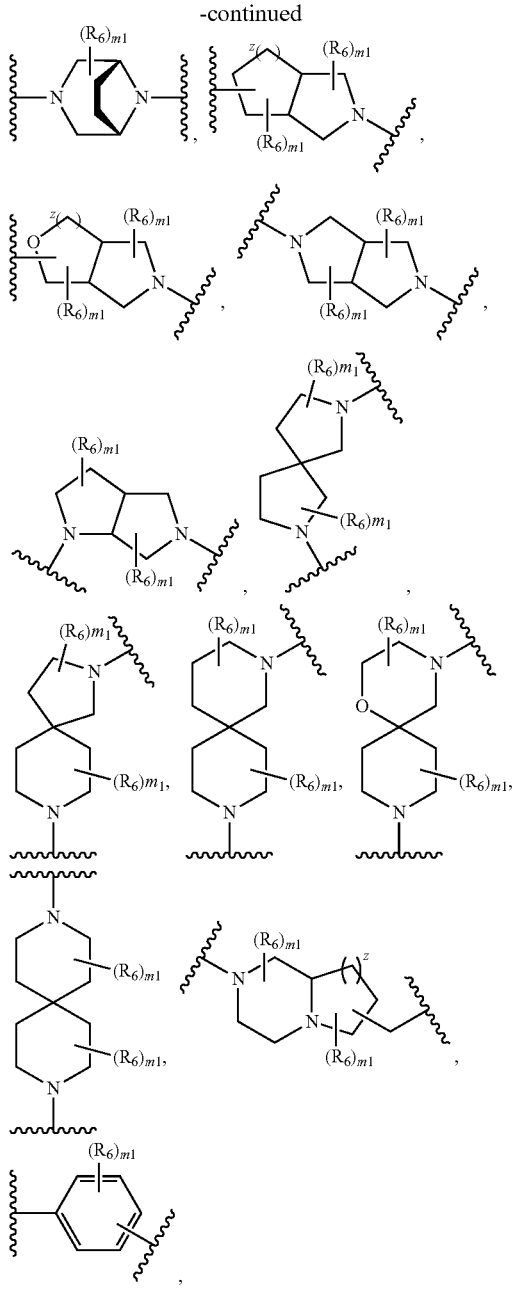

wherein the representation of L is not limited directionally left to right as is depicted, rather either the left side or the right side of L can be bound to the $W_1$ side of the compound of Formula I;

$R_6$ is independently —H, -D, —$C_1$-$C_4$ alkyl, -halogen, cyano, oxo, thiooxo, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;

each g is independently 2, 3 or 4;
each h is independently 1, 2, 3 or 4;
m is 0, 1, 2, 3, 4 or 5; if m is more than 1, then L can be the same or different;
m1 is 0, 1, 2 or 3;
k is 0, 1, 2, or 3;
z is 1, 2, or 3;
each $R_3$ is independently H or $C_1$-$C_6$ alkyl that can be optionally substituted with either O or N and in $NR_3R_3$, both $R_3$ when taken together with the nitrogen to which they are attached can form a heterocyclic ring such as a pyrrolidine, piperidine, morpholine, piperazine or pyrrole;

each $R_4$ independently e, H or straight or branched $C_1$-$C_{10}$ alkyl which can be optionally substituted with OH, $NH_2$, $CO_2R$, $CONH_2$, phenyl, $C_6H_4OH$, imidazole or arginine;

each e is independently H or any one of the side chains of the naturally occurring amino acids;

each Z is independently —H,

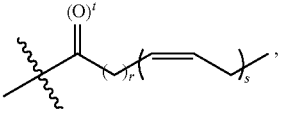

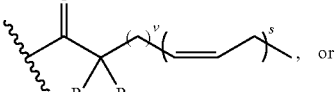, or

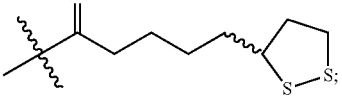

with the proviso that there is at least one of

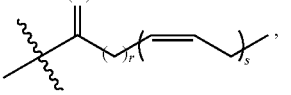

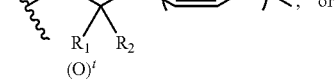, or

in the compound;
each r is independently 2, 3, or 7;
each s is independently 3, 5, or 6;
each t is independently 0 or 1;
each v is independently 1, 2, or 6;
$R_1$ and $R_2$ are independently —H, -D, —$C_1$-$C_4$ alkyl, -halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl; and each R is independently —H, —$C_1$-$C_3$ alkyl, or straight or branched $C_1$-$C_4$ alkyl optionally substituted with OH, or halogen;

In Formula I and Ia any one or more of H may be substituted with a deuterium. It is also understood in Formula I and Ia that a methyl substituent can be substituted with a $C_1$-$C_6$ alkyl.

Also described are pharmaceutical formulations comprising at least one fatty acid lenalidomide derivative.

Also described herein are methods of treating a disease susceptible to treatment with a fatty acid lenalidomide derivative in a patient in need thereof by administering to the patient an effective amount of a fatty acid lenalidomide derivative.

Also described herein are methods of treating metabolic diseases by administering to a patient in need thereof an effective amount of a fatty acid lenalidomide derivative.

The invention also includes pharmaceutical compositions that comprise an effective amount of a fatty acid lenalidomide derivative and a pharmaceutically acceptable carrier. The compositions are useful for treatment or prevention of multiple myeloma, myelodysplastic syndromes (MDS) or other metabolic diseases including including diabetic nephropathy, chronic kidney disease (CKD), atherosclerosis, dyslipidemia, coronary heart disease, hypercholesterimia, Type 2 diabetes, elevated cholesterol, metabolic syndrome and cardiovascular disease. In addition, they are useful in the treatment of autoimmune diseases such as rheumatoid arthritis, cystic fibrosis, inflammatory bowel diseases (including colitis and Crohn's disease). The invention includes a fatty acid lenalidomide derivative provided as a pharmaceutically acceptable prodrug, a hydrate, a salt, enantiomer, stereoisomer, or mixtures thereof.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

DETAILED DESCRIPTION OF THE INVENTION

The fatty acid lenalidomide derivatives have been designed to bring together lenalidomide analogs and omega-3 fatty acids into a single molecular conjugate. The activity of the fatty acid lenalidomide derivatives is substantially greater than the sum of the individual components of the molecular conjugate, suggesting that the activity induced by the fatty acid lenalidomide derivatives is synergistic.

DEFINITIONS

The following definitions are used in connection with the fatty acid lenalidomide derivatives:

The term "fatty acid lenalidomide derivatives" includes any and all possible isomers, stereoisomers, enantiomers, diastereomers, tautomers, pharmaceutically acceptable salts, hydrates, solvates, and prodrugs of the fatty acid lenalidomide derivatives described herein.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

Unless otherwise specifically defined, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. The substituents can themselves be optionally substituted.

"$C_1$-$C_3$ alkyl" refers to a straight or branched chain saturated hydrocarbon containing 1-3 carbon atoms. Examples of a $C_1$-$C_3$ alkyl group include, but are not limited to, methyl, ethyl, propyl and isopropyl.

"$C_1$-$C_4$ alkyl" refers to a straight or branched chain saturated hydrocarbon containing 1-4 carbon atoms. Examples of a $C_1$-$C_4$ alkyl group include, but are not limited to, methyl, ethyl, propyl, butyl, isopropyl, isobutyl, sec-butyl and tert-butyl.

"$C_1$-$C_5$ alkyl" refers to a straight or branched chain saturated hydrocarbon containing 1-5 carbon atoms. Examples of a $C_1$-$C_5$ alkyl group include, but are not limited to, methyl, ethyl, propyl, butyl, pentyl, isopropyl, isobutyl, sec-butyl and tert-butyl, isopentyl and neopentyl.

"$C_1$-$C_6$ alkyl" refers to a straight or branched chain saturated hydrocarbon containing 1-6 carbon atoms. Examples of a $C_1$-$C_6$ alkyl group include, but are not limited to, methyl, ethyl, propyl, butyl, pentyl, hexyl, isopropyl, isobutyl, sec-butyl, tert-butyl, isopentyl, and neopentyl.

The term "cycloalkyl" refers to a cyclic hydrocarbon containing 3-6 carbon atoms. Examples of a cycloalkyl group include, but are not limited to, cyclopropyl, cyclobutyl, cyclopentyl and cyclohexyl.

It is understood that any of the substitutable hydrogens on an alkyl or cycloalkyl can be substituted with halogen, $C_1$-$C_3$ alkyl, hydroxyl, alkoxy and cyano groups.

The term "heterocycle" as used herein refers to a cyclic hydrocarbon containing 3-6 atoms wherein at least one of the atoms is an O, N, or S. Examples of heterocycles include, but are not limited to, aziridine, oxirane, thiirane, azetidine, oxetane, thietane, pyrrolidine, tetrahydrofuran, tetrahydrothiophene, piperidine, tetrahydropyran, thiane, imidazolidine, oxazolidine, thiazolidine, dioxolane, dithiolane, piperazine, oxazine, dithiane, and dioxane.

The term "any one of the side chains of the naturally occurring amino acids" as used herein means a side chain of any one of the following amino acids: Isoleucine, Alanine, Leucine, Asparagine, Lysine, Aspartate, Methionine, Cysteine, Phenylalanine, Glutamate, Threonine, Glutamine, Tryptophan, Glycine, Valine, Proline, Arginine, Serine, Histidine and Tyrosine.

The term "fatty acid" as used herein means an omega-3 fatty acid and fatty acids that are metabolized in vivo to omega-3 fatty acids. Non-limiting examples of fatty acids are all-cis-7,10,13-hexadecatrienoic acid, α-linolenic acid (ALA or all-cis-9,12,15-octadecatrienoic acid), stearidonic acid (STD or all-cis-6,9,12,15-octadecatetraenoic acid), eicosatrienoic acid (ETE or all-cis-11,14,17-eicosatrienoic acid), eicosatetraenoic acid (ETA or all-cis-8,11,14,17-eicosatetraenoic acid), eicosapentaenoic acid (EPA or all-cis-5,8,11,14,17-eicosapentaenoic acid), docosapentaenoic acid (DPA, clupanodonic acid or all-cis-7,10,13,16,19-docosapentaenoic acid), docosahexaenoic acid (DHA or all-cis-4,7,10,13,16,19-docosahexaenoic acid), tetracosapentaenoic acid (all-cis-9,12,15,18,21-docosahexaenoic acid), tetracosahexaenoic acid (nisinic acid or all-cis-6,9,12,15,18,21-tetracosenoic acid) or stereoisomers of lipoic acid.

The term "lenalidomide" as used herein means the molecule known as lenalidomide and any derivative thereof One such derivative is pomalidomide.

A "subject" is a mammal, e.g., a human, mouse, rat, guinea pig, dog, cat, horse, cow, pig, or non-human primate, such as a monkey, chimpanzee, baboon or rhesus, and the terms "subject" and "patient" are used interchangeably herein.

The invention also includes pharmaceutical compositions comprising an effective amount of a fatty acid lenalidomide derivative and a pharmaceutically acceptable carrier. The invention includes a fatty acid lenalidomide derivative provided as a pharmaceutically acceptable prodrug, hydrate, salt, such as a pharmaceutically acceptable salt, enantiomers, stereoisomers, or mixtures thereof.

Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide and valerate salts.

The term "metabolic disease" as used herein refers to disorders, diseases and syndromes involving dyslipidemia, and the terms metabolic disorder, metabolic disease, and metabolic syndrome are used interchangeably herein.

An "effective amount" when used in connection with a fatty acid lenalidomide derivative is an amount effective for treating or preventing a metabolic disease.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The term "treating", with regard to a subject, refers to improving at least one symptom of the subject's disorder. Treating can be curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a fatty acid lenalidomide derivative.

The following abbreviations are used herein and have the indicated definitions: Boc and BOC are tert-butoxycarbonyl, Boc$_2$O is di-tert-butyl dicarbonate, BSA is bovine serum albumin, CDI is 1,1'-carbonyldiimidazole, DCC is N,N'-dicyclohexylcarbodiimide, DIEA is N,N-diisopropylethylamine, DMAP is 4-dimethylaminopyridine, DMEM is Dulbecco's Modified Eagle Medium, DMF is N,N-dimethylformamide, DOSS is sodium dioctyl sulfosuccinate, EDC and EDCI are 1-ethyl-3-(3-dimethylaminopropyl)carbodiimide hydrochloride, ELISA is enzyme-linked immunosorbent assay, EtOAc is ethyl acetate, FBS is fetal bovine serum, h is hour, HATU is 2-(7-aza-1H-benzotriazole-1-yl)-1,1,3,3-tetramethyluronium hexafluorophosphate, HIV is human immunodeficiency virus, HPMC is hydroxypropyl methylcellulose, oxone is potassium peroxymonosulfate, Pd/C is palladium on carbon, TFA is trifluoroacetic acid, TGPS is tocopherol propylene glycol succinate, and THF is tetrahydrofuran.

Compounds

Accordingly in one aspect, the present invention provides a molecular conjugate which comprises a lenalidomide and a fatty acid covalently linked, wherein the fatty acid is selected from the group consisting of omega-3 fatty acids and fatty acids that are metabolized in vivo to omega-3 fatty acids, wherein the conjugate comprises at least one amide and the conjugate is capable of hydrolysis to produce free lenalidomide and free fatty acid.

In some embodiments, the fatty acid is selected from the group consisting of all-cis-7,10,13-hexadecatrienoic acid, α-linolenic acid, stearidonic acid, eicosatrienoic acid, eicosatetraenoic acid, eicosapentaenoic acid (EPA), docosapentaenoic acid, docosahexaenoic acid (DHA), tetracosapentaenoic acid, tetracosahexaenoic acid and lipoic acid. In other embodiments, the fatty acid is selected from eicosapentaenoic acid, docosahexaenoic acid and lipoic acid. In some embodiments, the hydrolysis is enzymatic.

In another aspect, the present invention provides fatty acid lenalidomide derivatives according to Formula I and Ia:

Formula I

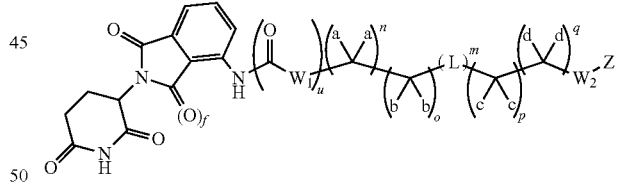

Formula Ia

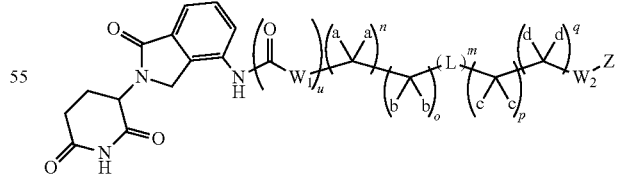

and pharmaceutically acceptable salts, hydrates, solvates, prodrugs, enantiomers and stereoisomers thereof;

wherein $R_1$, $R_2$, $R_3$, $W_1$, $W_2$, L, a, c, b, d, e, f, g, h, m, n, o, p, q, Z, r, s, t, u, v, $R_4$, $R_6$, and R are as defined above for Formula I and Ia, In some embodiments, one Z is

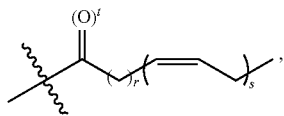

and r is 2.

In some embodiments, one Z is

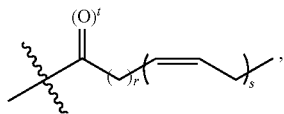

and r is 3.

In some embodiments, one Z is

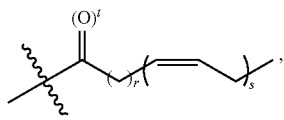

and r is 7.

In other embodiments, one Z is

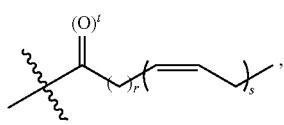

and s is 3.

In some embodiments, one Z is

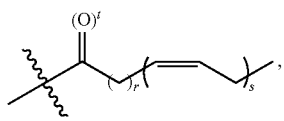

and s is 5.

In some embodiments, one Z is

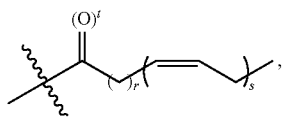

and s is 6.

In some embodiments, one Z is

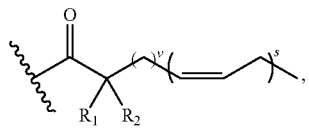

and v is 1.

In other embodiments, one Z is

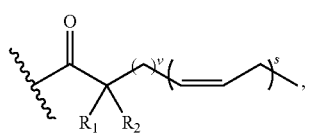

and v is 2.

In some embodiments, one Z is

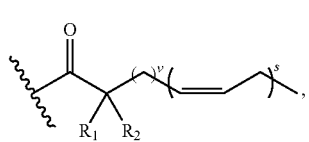

and v is 6.

In some embodiments, one Z is

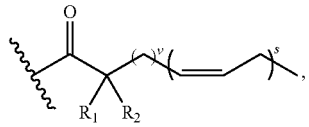

and s is 3.

In some embodiments, one Z is

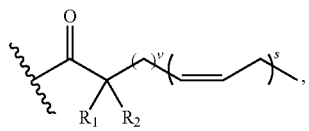

and s is 5.

In other embodiments, one Z is

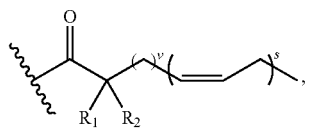

and s is 6.

In other embodiments, Z is

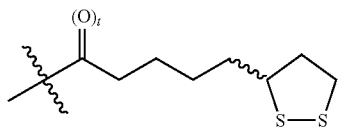

and t is 1.

In some embodiments, Z is

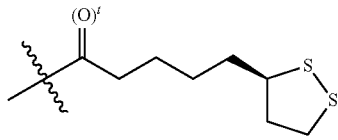

and t is 1.

In some embodiments, $W_1$ is NH.
In some embodiments, $W_2$ is NH.
In some embodiments, $W_1$ is O.
In some embodiments, $W_2$ is O.
In some embodiments, $W_1$ is null.
In some embodiments, $W_2$ is null.
In some embodiments, $W_1$ and $W_2$ are each NH.
In some embodiments, $W_1$ and $W_2$ are each null.
In some embodiments, $W_1$ is O and $W_2$ is NH.
In some embodiments, $W_1$ and $W_2$ are each NR, and R is $CH_3$.
In some embodiments, f is 0.
In some embodiments, f is 1.
In some embodiments, m is 0.
In other embodiments, m is 1.
In other embodiments, m is 2.
In some embodiments, L is —S— or —S—S—.
In some embodiments, L is —O—.
In some embodiments, L is —C(O)—.
In some embodiments, L is heteroaryl.
In some embodiments, L is heterocycle.
In some embodiments, L is

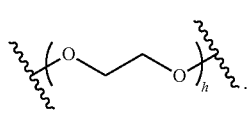

In some embodiments, L is

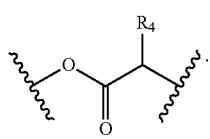

In some embodiments, L is

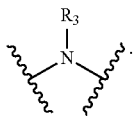

In some embodiments, L is

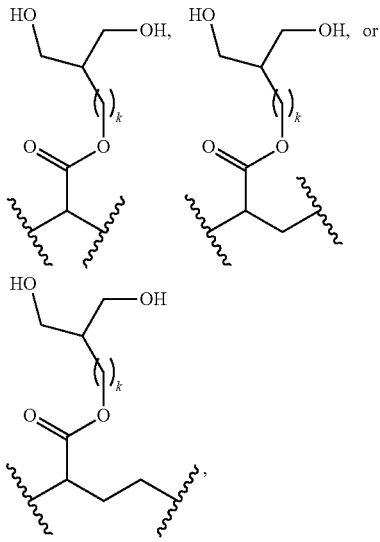

In some embodiments, L is

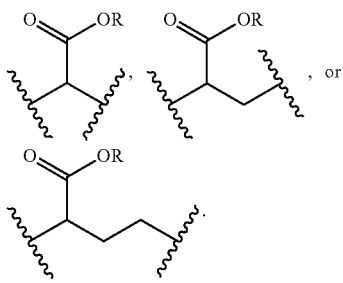

In some embodiments, L is

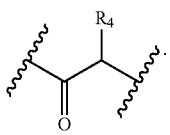

In some embodiments, L is

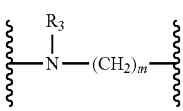

wherein m is 2.

In some embodiments, L is
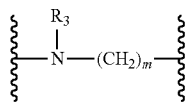
wherein m is 3.
In some embodiments, L is
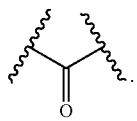 [SMILES: *C(*)=O]
In some embodiments, L is
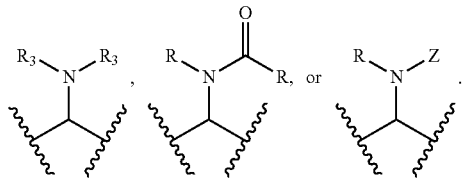
In some embodiments, L is
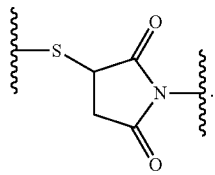 [SMILES: *SC1CC(=O)N(*)C1=O]
In some embodiments, L is
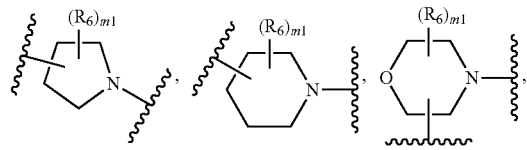
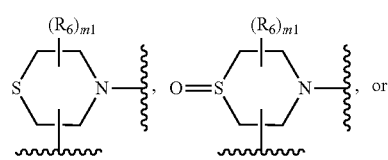
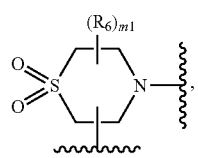
In some embodiments, L is
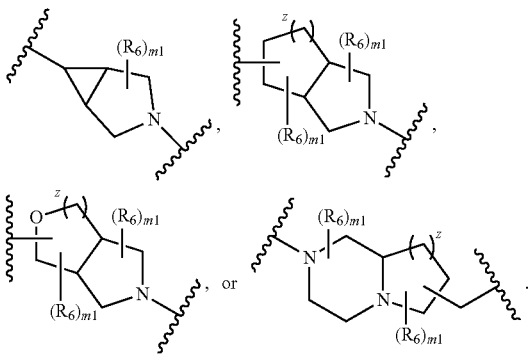
In some embodiments, L is
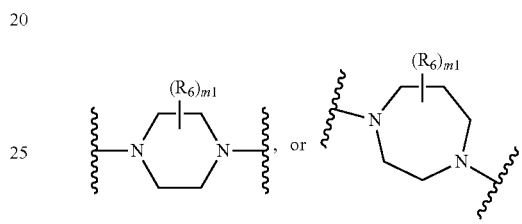
In some embodiments, L is
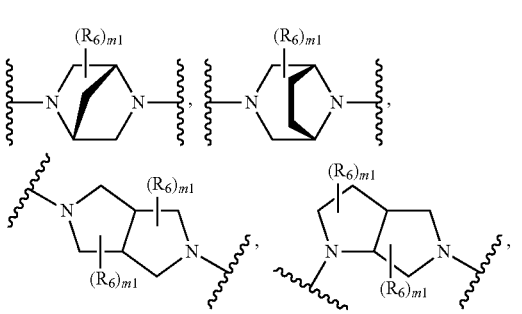
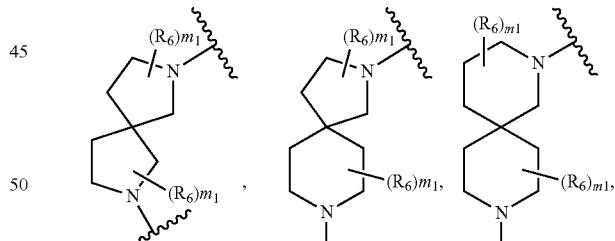
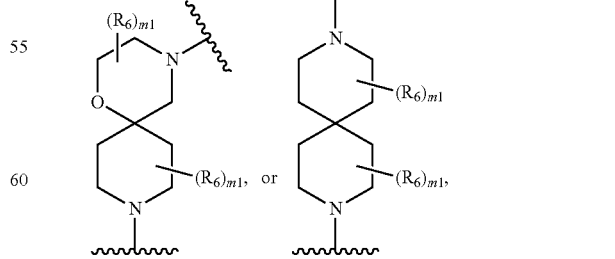
In other embodiments, one of n, o, p, and q is 1.
In some embodiments, two of n, o, p, and q are each 1.
In other embodiments, three of n, o, p, and q are each 1.

In some embodiments n, o, p, and q are each 1.

In some embodiments, one d is C(O)OR.

In some embodiments, r is 2 and s is 6.

In some embodiments, r is 3 and s is 5.

In some embodiments, t is 1.

In some embodiments, $W_1$ and $W_2$ are each NH, m is 0, n, and o are each 1, and p and q are each 0.

In some embodiments, $W_1$ and $W_2$ are each NH, m is 1, n, o, p, and q are each 1, and L is O.

In some embodiments, $W_1$ and $W_2$ are each NH, m is 1, n, o, p, and q are each 1, and L is

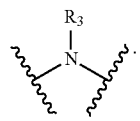

In some embodiments, $W_1$ and $W_2$ are each NH, m is 1, n, o, p, and q are each 1, and L is —S—S—.

In some embodiments, $W_1$ and $W_2$ are each NH, m is 1, n and o are each 0, p and q are each 1, and L is

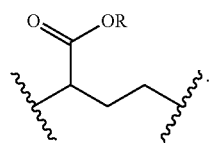

In some embodiments, $W_1$ and $W_2$ are each NH, m is 1, k is 0, n and o are each 0, p and q are each 1, and L is

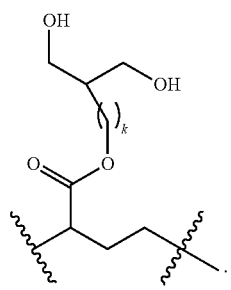

In some embodiments, $W_1$ and $W_2$ are each NH, m is 1, n and o are each 1, p and q are each 0, and L is

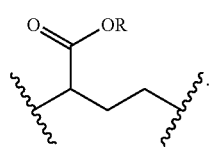

In some embodiments, $W_1$ and $W_2$ are each NH, m is 1, k is 0, n is 1, o, p and q are each 0, and L is

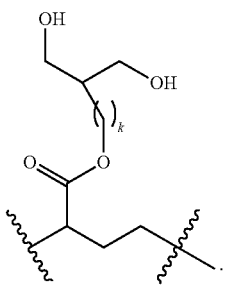

In some embodiments, $W_1$ and $W_2$ are each NH, m is 1, n, o, and p are each 0, and q is 1, and L is

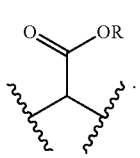

In some embodiments, $W_1$ and $W_2$ are each NH, m is 1, k is 1, n, o, and p are each 0, and q is 1, and L is

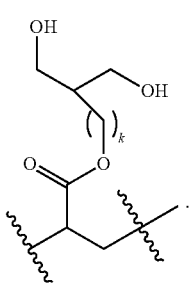

In some embodiments, $W_1$ and $W_2$ are each NH, m is 1, n is 1, and o, p, and q are each 0, and L is

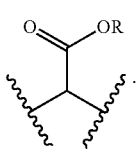

In some embodiments, $W_1$ and $W_2$ are each NH, m is 1, k is 1, o, p, and q are each 0, and L is

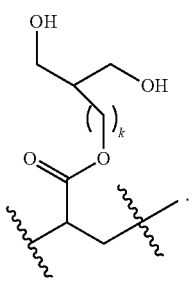

In some embodiments, $W_1$ and $W_2$ are each NH, m is 1, n, o, p, and q are each 1, and L is

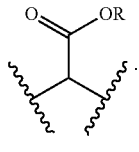

In some embodiments, $W_1$ and $W_2$ are each NH, m is 1, n, o, p, and q are each 1, and L is

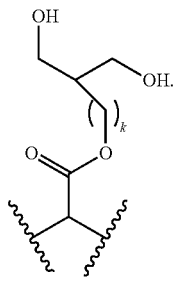

In some embodiments, $W_1$ and $W_2$ are each NH, m is 0, k is 1, o and p are each 1, and q is 0.

In some embodiments, $W_1$ and $W_2$ are each NH, m is 0, n, o, p, and q are each 1.

In some embodiments, $W_1$ and $W_2$ are each NH, m is 0, n and o are each 1, p and q are each 0, and each a is $CH_3$.

In some embodiments, $W_1$ and $W_2$ are each NH, m is 0, n and o are each 1, p and q are each 0, and each b is $CH_3$.

In some embodiments, $W_1$ and $W_2$ are each NH, m is 1, n, o, p, and q are each 1, $R_3$ is H, and L is

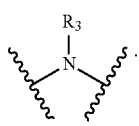

In some embodiments, $W_1$ and $W_2$ are each NH, m is 1, n, p and q are each 1, and o is 2, $R_3$ is H, and L is

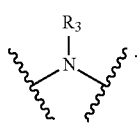

In some embodiments, $W_1$ and $W_2$ are each NH, m is 1, n, o, p are each 1, and q is 2, and L is

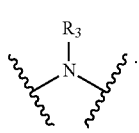

In some embodiments, $W_1$ and $W_2$ are each NH, m is 1, n, o, p, and q are each 1, and L is

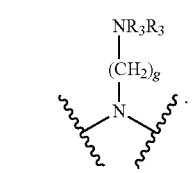

In some embodiments, $W_1$ and $W_2$ are each NH, m is 1, n and p are each 1, and o and q are each 0, and L is —C(O)—.

In some embodiments, $W_1$ and $W_2$ are each NH, m is 1, n and p are each 1, and o, and q are each 0, and L is

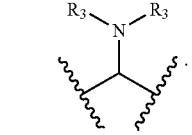

In some embodiments, $W_1$ and $W_2$ are each NH, m is 1, n, o, p, q are each 1, and L is

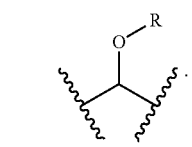

In some embodiments, $W_1$ and $W_2$ are each NH, m is 1, n, o, p, and q are each 1, h is 1, and L is

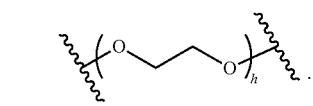

In some embodiments, $W_1$ and $W_2$ are each NH, m is 1, n, o, p, and q are each 1, and L is —S—.

In some embodiments, $W_1$ and $W_2$ are each NH, m is 1, n, o, p are each 0, q is 1, one d is —$CH_3$, and L is

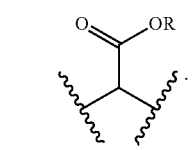

In some embodiments, $W_1$ and $W_2$ are each NH, m is 2, n, o, p, and q are each 0, one L is

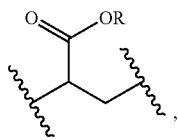, and one L is

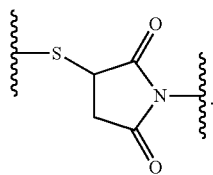 [SMILES: *SC1CC(=O)N(*)C1=O]

In some embodiments, m is 0, n, o, p, and q are each 0, and $W_1$ and $W_2$ are taken together to form an optionally substituted piperazine group.

In some embodiments, m is 1, n, o, p, and q are each 0, $W_1$ and $W_2$ are each null, and L is

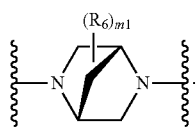

In some embodiments, m is 1, n and p are each 1, o and q are each 0, $W_1$ and $W_2$ are each NH, and L is $C_3$-$C_6$ cycloalkyl.

In some embodiments, m is 1, n is 1, o, p, and q are each 0, $W_1$ and $W_2$ are each NH, and L is $C_3$-$C_6$ cycloalkyl.

In some embodiments, m is 1, n, o, p, are each 0, q is 1, $W_1$ and $W_2$ are each NH, and L is $C_3$-$C_6$ cycloalkyl.

In some embodiments, m is 1, n, o, p, and q are each 0, $W_1$ is NH, $W_2$ is null, and L is

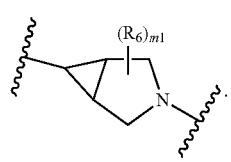

In some embodiments, m is 1, n o, p, and q are each 0, $W_1$ is null, $W_2$ is NH, and L is

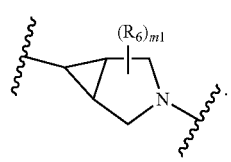

In some embodiments, m is 1, n o, p, and q are each 0, $W_1$ is NH, $W_2$ is null, and L is

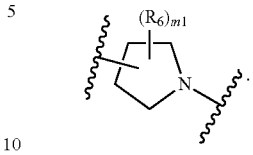

In some embodiments, m is 1, n o, p, and q are each 0, $W_1$ is null, $W_2$ is NH, and L is

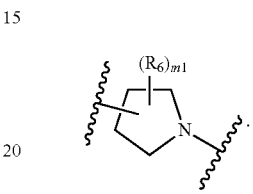

In some embodiments, m is 1, n is 1, o, p, and q are each 0, $W_1$ is NH, $W_2$ is null, and L is

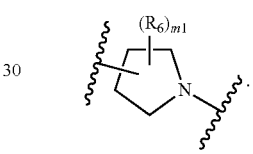

In some embodiments, m is 1, n, o, p, are each 0, q is 1, $W_1$ is null, $W_2$ is NH, and L is

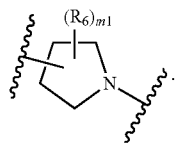

In some embodiments, m is 1, n, o, p, and q are each 0, $W_1$ is NH, $W_2$ is null, and L is

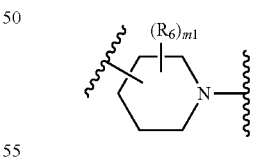

In some embodiments, m is 1, n, o, p, and q are each 0, $W_1$ is null, $W_2$ is NH, and L is

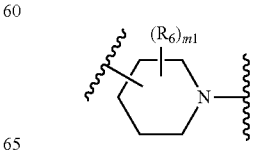

In some embodiments, m is 1, n is 1, o, p, and q are each 0, $W_1$ is NH, $W_2$ is null, and L is

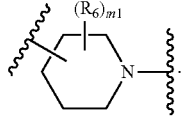

In some embodiments, m is 1, n, o, p, are each 0, q is 1, $W_1$ is null, $W_2$ is NH, and L is

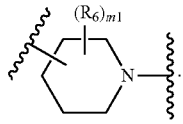

In some embodiments, m is 1, n is 1, o, p, and q are each 0, $W_1$ is NH, $W_2$ is null, and L is

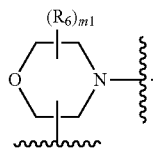

In some embodiments, m is 1, n, o, p, are each 0, q is 1, $W_1$ is null, $W_2$ is NH, and L is

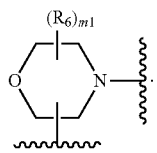

In some embodiments, m is 1, n, o, p, q are each 0, $W_1$ and $W_2$ is null, and L is

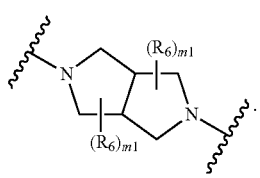

In some embodiments, m is 1, n, o, p, q are each 0, $W_1$ and $W_2$ is null, and L is

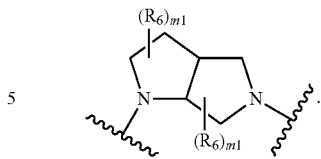

In some embodiments, m is 1, n, o, p, q are each 0, $W_1$ is NH, $W_2$ is null, and L is

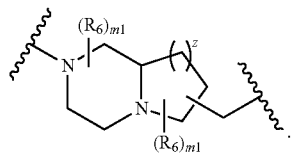

In some embodiments, m is 1, n, o, p, q are each 0, $W_1$ is null, $W_2$ is NH, and L is

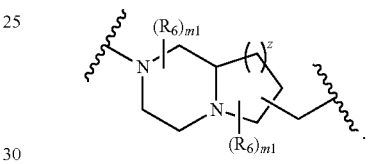

In some embodiments, m is 1, n, o, p, are each 0, q is 1, $W_1$ and $W_2$ are each and NH, is null, L is

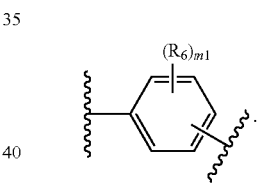

In some embodiments, m is 1, n, o, p, are each 0, q is 1, $W_1$ and $W_2$ are each NH, is null, and L is a heteroaryl.

In some of the foregoing embodiments, r is 2, s is 6 and t is 1.

In some of the foregoing embodiments, r is 3, s is 5 and t is 1.

In Formula I and Ia any one or more of H may be substituted with a deuterium. It is also understood in Formula I and Ia that a methyl substituent can be substituted with a $C_1$-$C_6$ alkyl.

In other illustrative embodiments, compounds of Formula I are as set forth below:

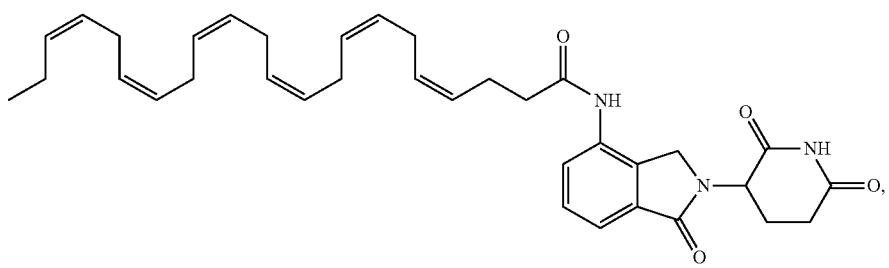 [SMILES: CC/C=C\C/C=C\C/C=C\C/C=C\C/C=C\C/C=C\CCC(=O)Nc1cccc2c1CN(C1CCC(=O)NC1=O)C2=O]

(4Z,7Z,10Z,13Z,16Z,19Z)-N-(2-(2,6-dioxopiperidin-3-yl)-1-oxoisoindolin-4-yl)docosa-4,7,10,13,16,19-hexaenamide (I-1)
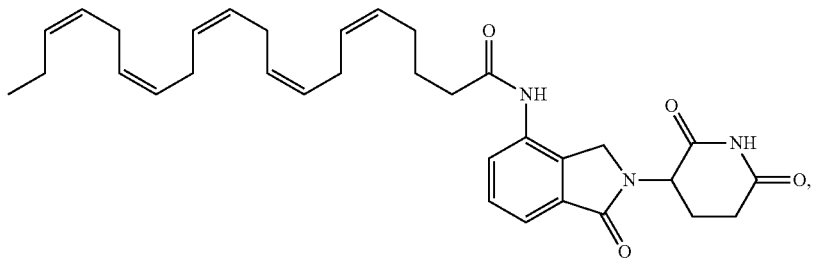 [SMILES: CC/C=C\C/C=C\C/C=C\C/C=C\C/C=C\CCCC(=O)Nc1cccc2c1CN(C1CCC(=O)NC1=O)C2=O]
(5Z,8Z,11Z,14Z,17Z)-N-(2-(2,6-dioxopiperidin-3-yl)-1-oxoisoindolin-4-yl)eicosa-5,8,11,14,17-pentaenamide (I-2)
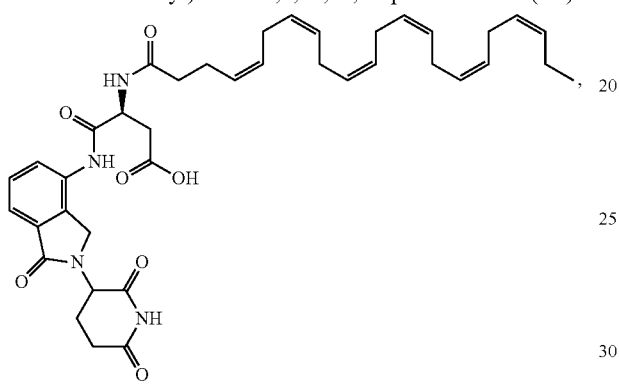
(S)-4-(2-(2,6-dioxopiperidin-3-yl)-1-oxoisoindolin-4-ylamino)-3-((4Z,7Z,10Z,13Z,16Z,19Z)-docosa-4,7,10,13,16,19-hexaenamido)-4-oxobutanoic acid (I-3)
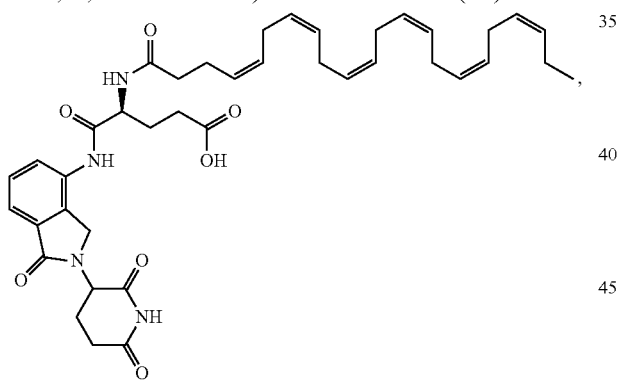
(S)-5-(2-(2,6-dioxopiperidin-3-yl)-1-oxoisoindolin-4-ylamino)-4-((4Z,7Z,10Z,13Z,16Z,19Z)-docosa-4,7,10,13,16,19-hexaenamido)-5-oxopentanoic acid (I-4)
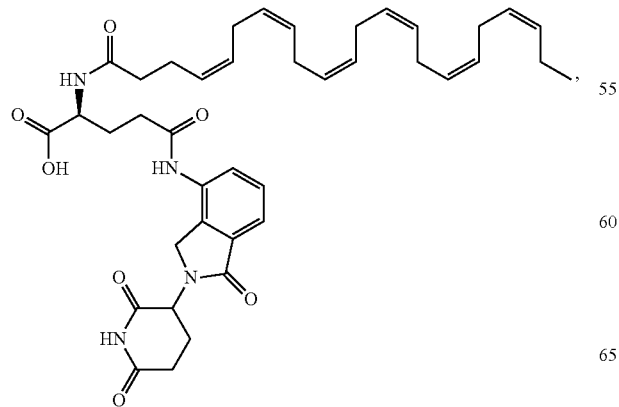

(S)-5-(2-(2,6-dioxopiperidin-3-yl)-1-oxoisoindolin-4-ylamino)-2-((4Z,7Z,10Z,13Z,16Z,19Z)-docosa-4,7,10,13,16,19-hexaenamido)-5-oxopentanoic acid (I-5)

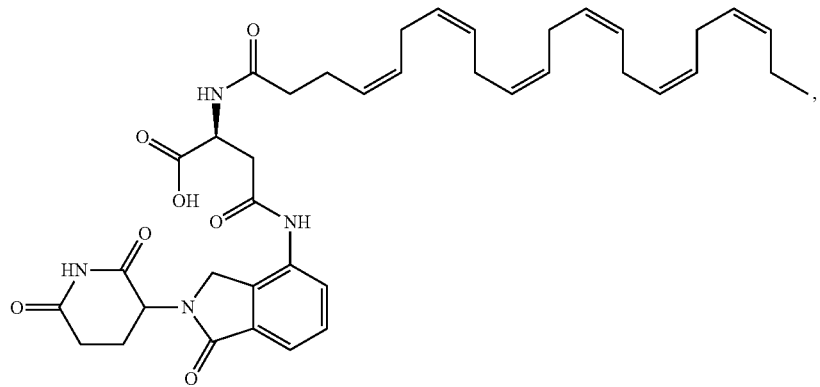 [SMILES: CC/C=C\C/C=C\C/C=C\C/C=C\C/C=C\C/C=C\CCC(=O)N[C@@H](CC(=O)Nc1cccc2c1CN(C1CCC(=O)NC1=O)C2=O)C(=O)O]

(S)-2-((4Z,7Z,10Z,13Z,16Z,19Z)-docosa-4,7,10,13,16,19-hexaenamido)-4-((3-hydroxy-5-(hydroxymethyl)-2-methylpyridin-4-yl)methylamino)-4-oxobutanoic acid (I-6)

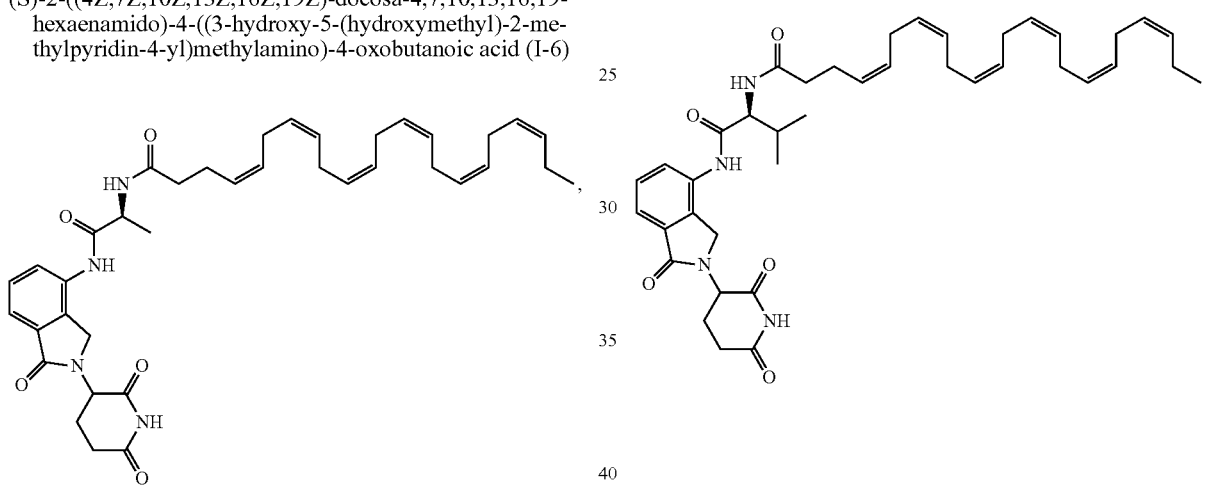

(4Z,7Z,10Z,13Z,16Z,19Z)-N-((2S)-1-((2-(2,6-dioxopiperidin-3-yl)-1-oxoisoindolin-4-yl)amino)-1-oxopropan-2-yl)docosa-4,7,10,13,16,19-hexaenamide (I-7)

(4Z,7Z,10Z,13Z,16Z,19Z)-N-((2S)-1-((2-(2,6-dioxopiperidin-3-yl)-1-oxoisoindolin-4-yl)amino)-3-methyl-1-oxobutan-2-yl)docosa-4,7,10,13,16,19-hexaenamide (I-8)

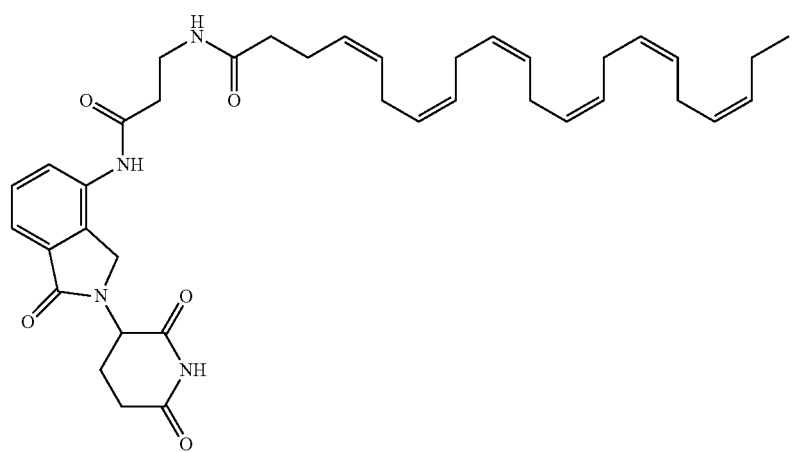 [SMILES: CC/C=C\C/C=C\C/C=C\C/C=C\C/C=C\C/C=C\CCC(=O)NCCC(=O)Nc1cccc2c1CN(C1CCC(=O)NC1=O)C2=O]

(4Z,7Z,10Z,13Z,16Z,19Z)-N-(3-((2-(2,6-dioxopiperidin-3-yl)-1-oxoisoindolin-4-yl)amino)-3-oxopropyl)docosa-4,7,10,13,16,19-hexaenamide (I-9)
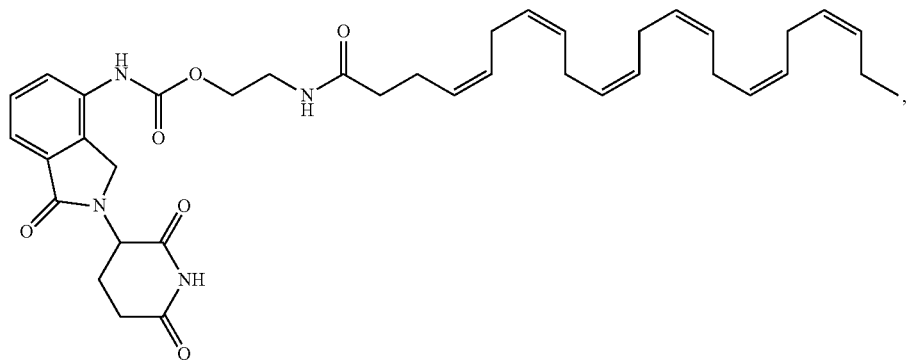 [SMILES: CC/C=C\C/C=C\C/C=C\C/C=C\C/C=C\C/C=C\CCC(=O)NCCOC(=O)Nc1cccc2c1CN(C1CCC(=O)NC1=O)C2=O]
2-(4Z,7Z,10Z,13Z,16Z,19Z)-docosa-4,7,10,13,16,19-hexaenamidoethyl 2-(2,6-dioxopiperidin-3-yl)-1-oxoisoindolin-4-ylcarbamate (I-10)
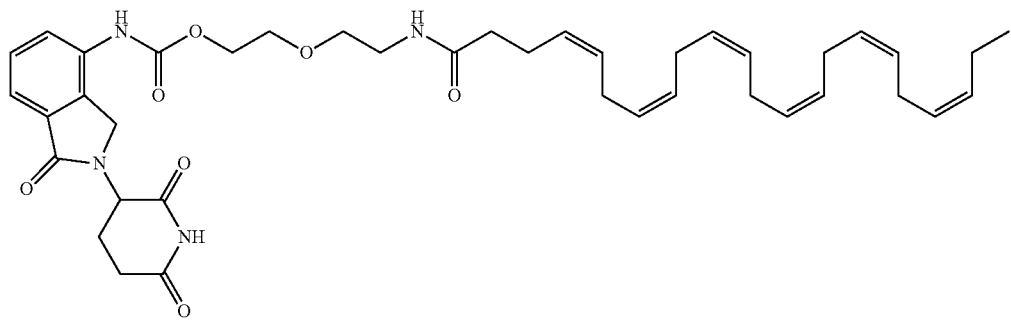 [SMILES: CC/C=C\C/C=C\C/C=C\C/C=C\C/C=C\C/C=C\CCC(=O)NCCOCCOC(=O)Nc1cccc2c1CN(C1CCC(=O)NC1=O)C2=O]
2-(2-((4Z,7Z,10Z,13Z,16Z,19Z)-docosa-4,7,10,13,16,19-hexaenamido)ethoxy)ethyl (2-(2,6-dioxopiperidin-3-yl)-1-oxoisoindolin-4-yl)carbamate (I-11)
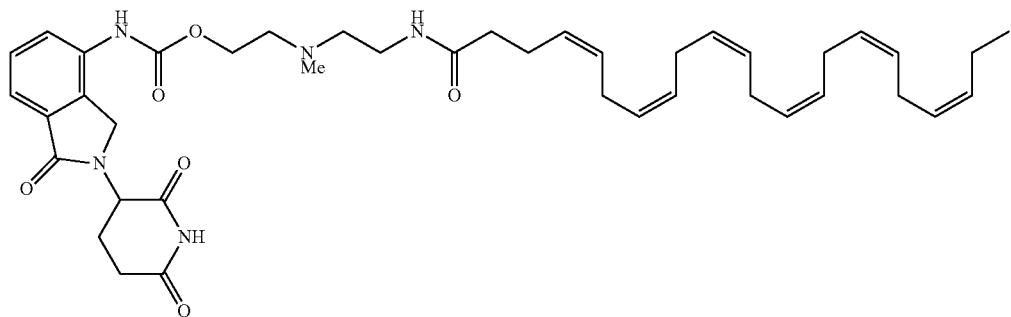 [SMILES: CC/C=C\C/C=C\C/C=C\C/C=C\C/C=C\C/C=C\CCC(=O)NCCN(C)CCOC(=O)Nc1cccc2c1CN(C1CCC(=O)NC1=O)C2=O]
2-((2-((4Z,7Z,10Z,13Z,16Z,19Z)-docosa-4,7,10,13,16,19-hexaenamido)ethyl)(methyl)amino)ethyl (2-(2,6-dioxopiperidin-3-yl)-1-oxoisoindolin-4-yl)carbamate (I-12)

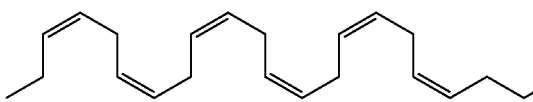
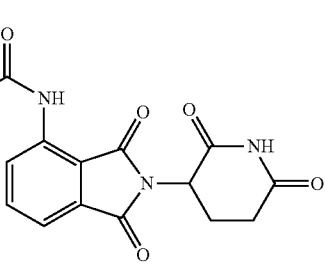

(4Z,7Z,10Z,13Z,16Z,19Z)-N-(2-(2,6-dioxopiperidin-3-yl)-1,3-dioxoisoindolin-4-yl)docosa-4,7,10,13,16,19-hexaenamide (I-13)

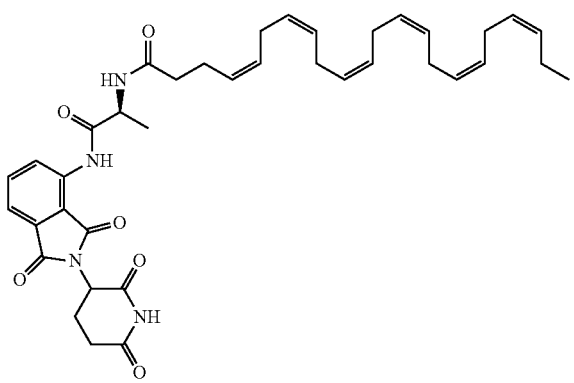

(4Z,7Z,10Z,13Z,16Z,19Z)-N-((2S)-1-((2-(2,6-dioxopiperidin-3-yl)-1,3-dioxoisoindolin-4-yl)amino)-1-oxopropan-2-yl)docosa-4,7,10,13,16,19-hexaenamide (I-14)

Methods for Using Fatty Acid Lenalidomide Derivatives

The invention includes methods for the treatment or prevention of multiple myeloma, myelodysplastic syndromes (MDS) or other metabolic diseases including diabetic nephropathy, chronic kidney disease (CKD), atherosclerosis, dyslipidemia, coronary heart disease, hypercholesterimia, Type 2 diabetes, elevated cholesterol, metabolic syndrome and cardiovascular disease. In addition, they are useful in the treatment of autoimmune diseases such as rheumatoid arthritis, cystic fibrosis, inflammatory bowel diseases (including colitis and Crohn's disease)

In one embodiment, the method comprises contacting a cell with a fatty acid lenalidomide derivative in an amount sufficient to improve renal function in type 1 or type 2 patients with diabetic nephropathy or patients with chronic kidney disease (CKD).

Also provided in the invention is a method for inhibiting, preventing, or treating a metabolic disease, or symptoms of a metabolic disease, in a subject. Examples of such disorders include, but are not limited to atherosclerosis, dyslipidemia, hypertriglyceridemia, hypertension, heart failure, cardiac arrhythmias, low HDL levels, high LDL levels, sudden death, stable angina, coronary heart disease, acute myocardial infarction, secondary prevention of myocardial infarction, cardiomyopathy, endocarditis, type 2 diabetes, insulin resistance, impaired glucose tolerance, hypercholesterolemia, stroke, hyperlipidemia, hyperlipoproteinemia, chronic kidney disease, intermittent claudication, hyperphosphatemia, carotid atherosclerosis, peripheral arterial disease, diabetic nephropathy, hypercholesterolemia in HIV infection, acute coronary syndrome (ACS), non-alcoholic fatty liver disease, arterial occlusive diseases, cerebral arteriosclerosis, cerebrovascular disorders, myocardial ischemia and diabetic autonomic neuropathy.

In some embodiments, the subject is administered an effective amount of a fatty acid lenalidomide derivative.

The invention also includes pharmaceutical compositions useful for treating or preventing a metabolic disease, or for inhibiting a metabolic disease, or more than one of these activities. The compositions can be suitable for internal use and comprise an effective amount of a fatty acid lenalidomide derivative and a pharmaceutically acceptable carrier. The fatty acid lenalidomide derivatives are especially useful in that they demonstrate very low peripheral toxicity or no peripheral toxicity.

The fatty acid lenalidomide derivatives can each be administered in amounts that are sufficient to treat or prevent a metabolic disease or prevent the development thereof in subjects.

Administration of the fatty acid lenalidomide derivatives can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising a fatty acid lenalidomide derivative and a pharmaceutically acceptable carrier, such as: a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, alginic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the fatty acid lenalidomide derivative is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the fatty acid lenalidomide derivatives.

The fatty acid lenalidomide derivatives can be also formulated as a suppository that can be prepared from fatty emulsions or suspensions; using polyalkylene glycols such as propylene glycol, as the carrier.

The fatty acid lenalidomide derivatives can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564, the contents of which are herein incorporated by reference in their entirety.

Fatty acid lenalidomide derivatives can also be delivered by the use of monoclonal antibodies as individual carriers to which the fatty acid lenalidomide derivatives are coupled. The fatty acid lenalidomide derivatives can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the fatty acid lenalidomide derivatives can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, fatty acid lenalidomide derivatives are not covalently bound to a polymer, e.g., a polycarboxylic acid polymer, or a polyacrylate.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 90%, from about 10% to about 90%, or from about 30% to about 90% of the fatty acid lenalidomide derivative by weight or volume.

The dosage regimen utilizing the fatty acid lenalidomide derivative is selected in accordance with a variety of factors including type, species, age, weight, sex and medical condition of the patient; the severity of the condition to be treated; the route of administration; the renal or hepatic function of the patient; and the particular fatty acid lenalidomide derivative employed. A physician or veterinarian of ordinary skill in the art can readily determine and prescribe the effective amount of the drug required to prevent, counter or arrest the progress of the condition.

Effective dosage amounts of the present invention, when used for the indicated effects, range from about 20 mg to about 5,000 mg of the fatty acid lenalidomide derivative per day. Compositions for in vivo or in vitro use can contain about 20, 50, 75, 100, 150, 250, 500, 750, 1,000, 1,250, 2,500, 3,500, or 5,000 mg of the fatty acid lenalidomide derivative. In one embodiment, the compositions are in the form of a tablet that can be scored. Effective plasma levels of the fatty acid lenalidomide derivative can range from about 5 ng/mL to 5,000 ng/mL. Appropriate dosages of the fatty acid lenalidomide derivatives can be determined as set forth in Goodman, L. S.; Gilman, A. *The Pharmacological Basis of Therapeutics,* 5th ed.; MacMillan: New York, 1975, pp. 201-226.

Fatty acid lenalidomide derivatives can be administered in a single daily dose, or the total daily dosage can be administered in divided doses of two, three or four times daily. Furthermore, fatty acid lenalidomide derivatives can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of the fatty acid lenalidomide derivative ranges from about 0.1% to about 15%, w/w or w/v.

Methods of Making

Methods for Making the Fatty Acid Lenalidomide Derivatives

Examples of synthetic pathways useful for making fatty acid lenalidomide derivatives of Formula I are set forth in the Examples below and generalized in Schemes 1-4.

Scheme 1

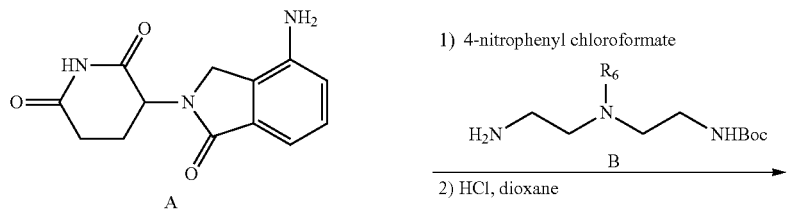

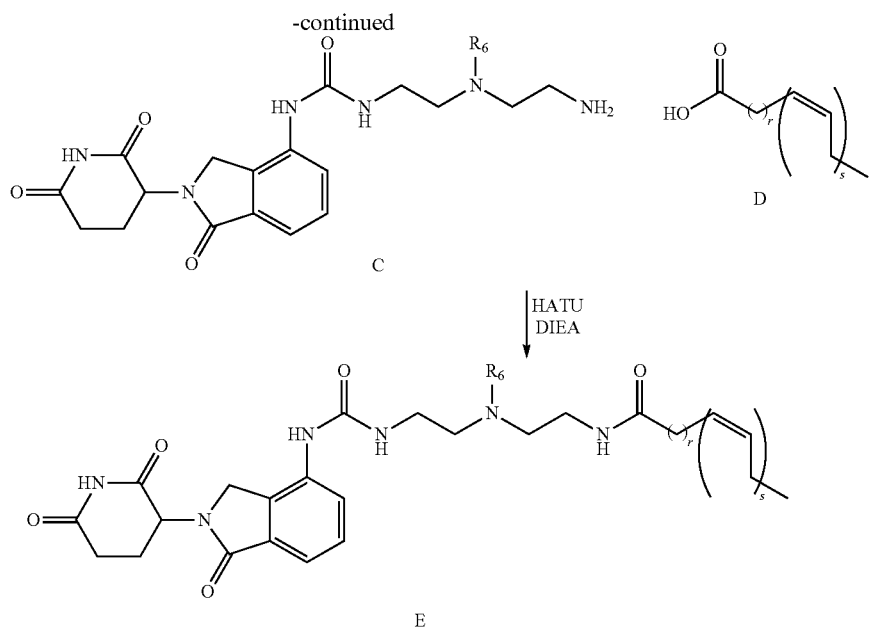

wherein $R_6$, $r$, and $s$ are as defined above.

The mono-BOC protected amine of the formula B can be obtained from commercial sources or prepared according to the procedures outlined in Krapcho et al. *Synthetic Commun.* 1990, 20, 2559-2564. Compound A (lenalidomide) can be reacted with 4-nitrophenyl chloroformate and then with the amine B in the presence of a tertiary amine base, followed by deprotection of the BOC group with acids such as TFA or HCl in a solvent such as $CH_2Cl_2$ or dioxane to produce the coupled compound C. Activation of compound C with a coupling agent such as HATU in the presence of an amine such as DIEA followed by addition of a fatty acid of formula D affords urea derivatives of the formula E. To those familiar in the art, pomalidomide can be used instead of compound A, lenalidomide. Also, to those familiar in the art, this same reaction sequence can also be carried out using the following substituted amines B1-B7 to obtain the corresponding urea derivatives of the formulas E1-E7. Detailed procedures, along with the references that are needed to prepare the corresponding amines B1-B7 are described in the following patent application: Vu et al "Preparation of fatty acid acylated salicylates for the treatment of inflammatory disorders" US 20100184730.

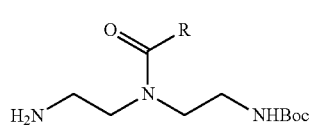

B1

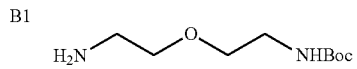

B2

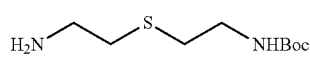

B3

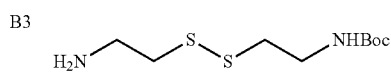

B4

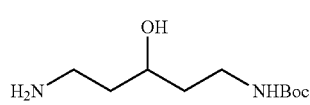

B5

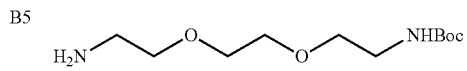

B6

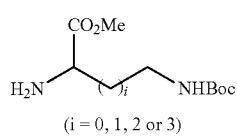

(i = 0, 1, 2 or 3)

B7

-continued
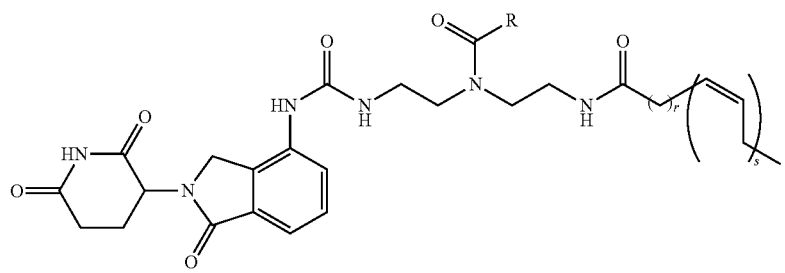
E1
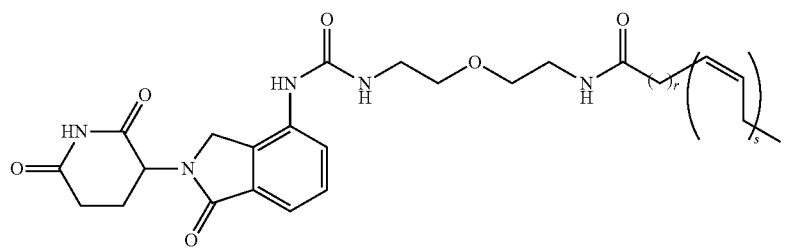
E2
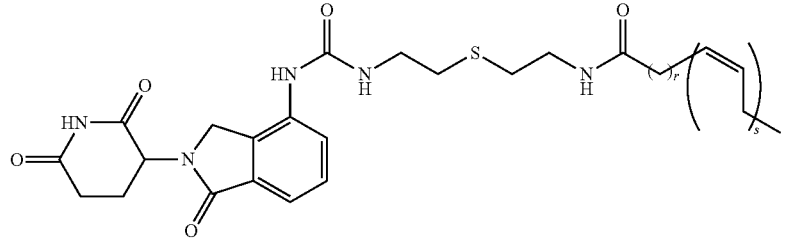
E3
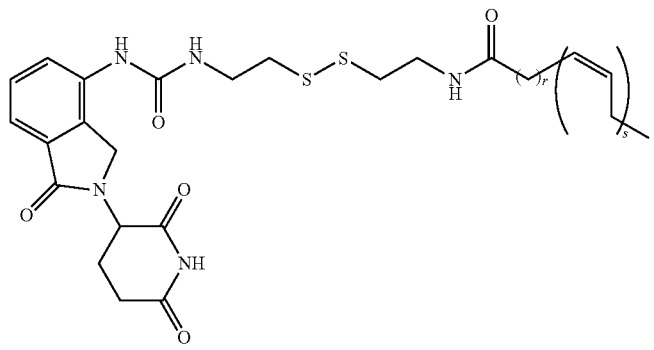
E4
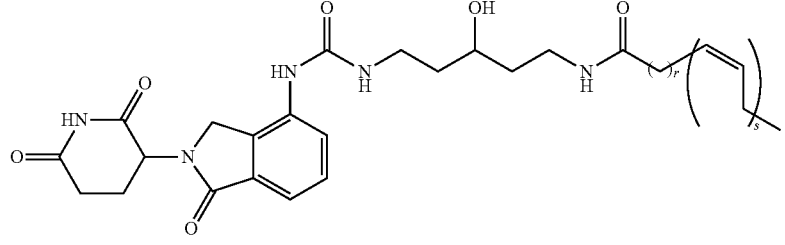
E5
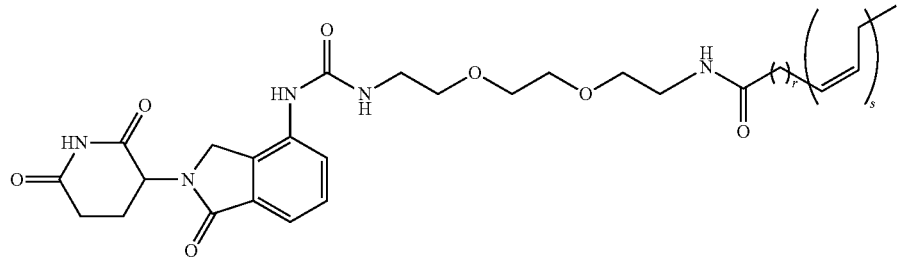
E6

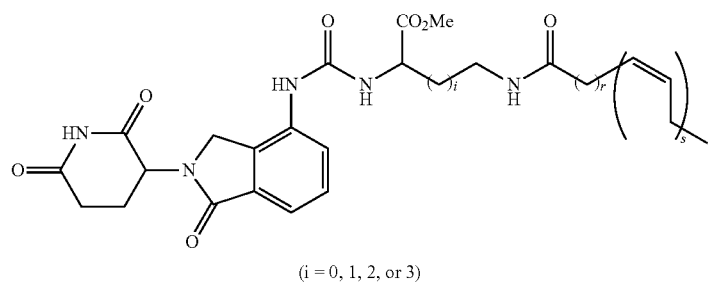
E7
(i = 0, 1, 2, or 3)
Scheme 2
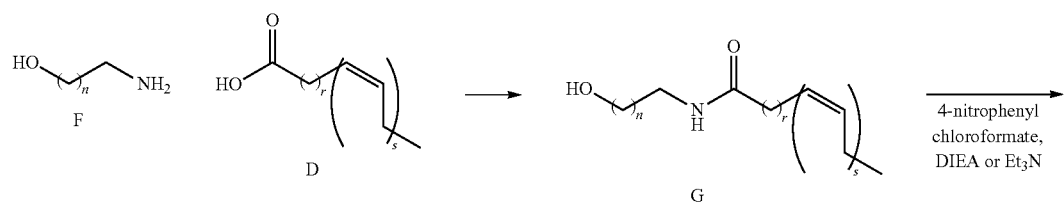
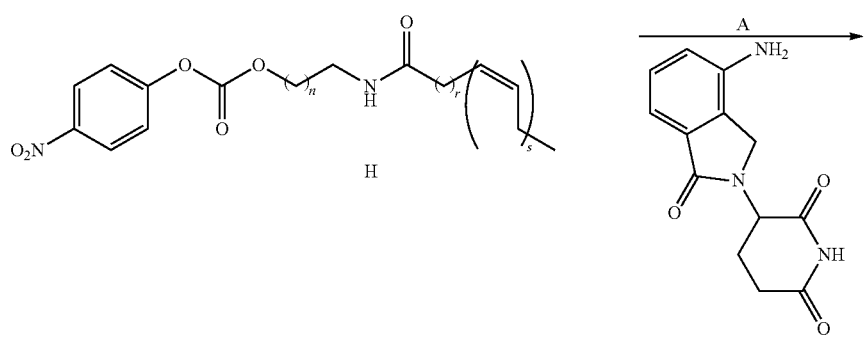
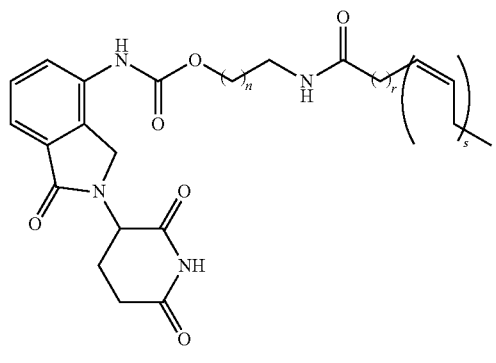
I The commercially available amine F (n=1, 2 or 3) is coupled with a fatty acid of the formula D in the presence of coupling reagent such as HATU or EDC, in a solvent such as dichloromethane or acetonitrile, to afford the amide of the formula G. Compound G is reacted with 4-nitrophenyl chloroformate in the presence of a tertiary amine such as DIEA or Et₃N, in a solvent such as dichloromethane or acetonitrile, to form compounds of the formula H. Compound H is treated with lenalidomide (formula A), in the presence of a tertiary amine such as DIEA or Et₃N, in acetonitrile or dichloromethane to afford compounds of the formula I.

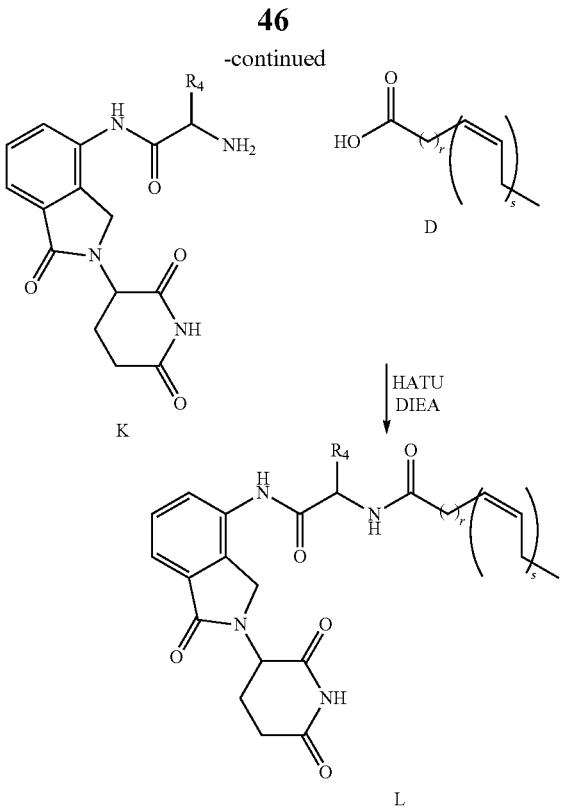

Lenalidomide (compound A) is coupled with a commercially available amino acid of the formula J in the presence of HATU/DIEA. The resulting product is then treated with acids such as HCl in dioxane or TFA in dichloromethane to afford compound K. Compound K is then coupled with a fatty acid of the formula D using HATU/DIEA to afford compounds of the formula L.

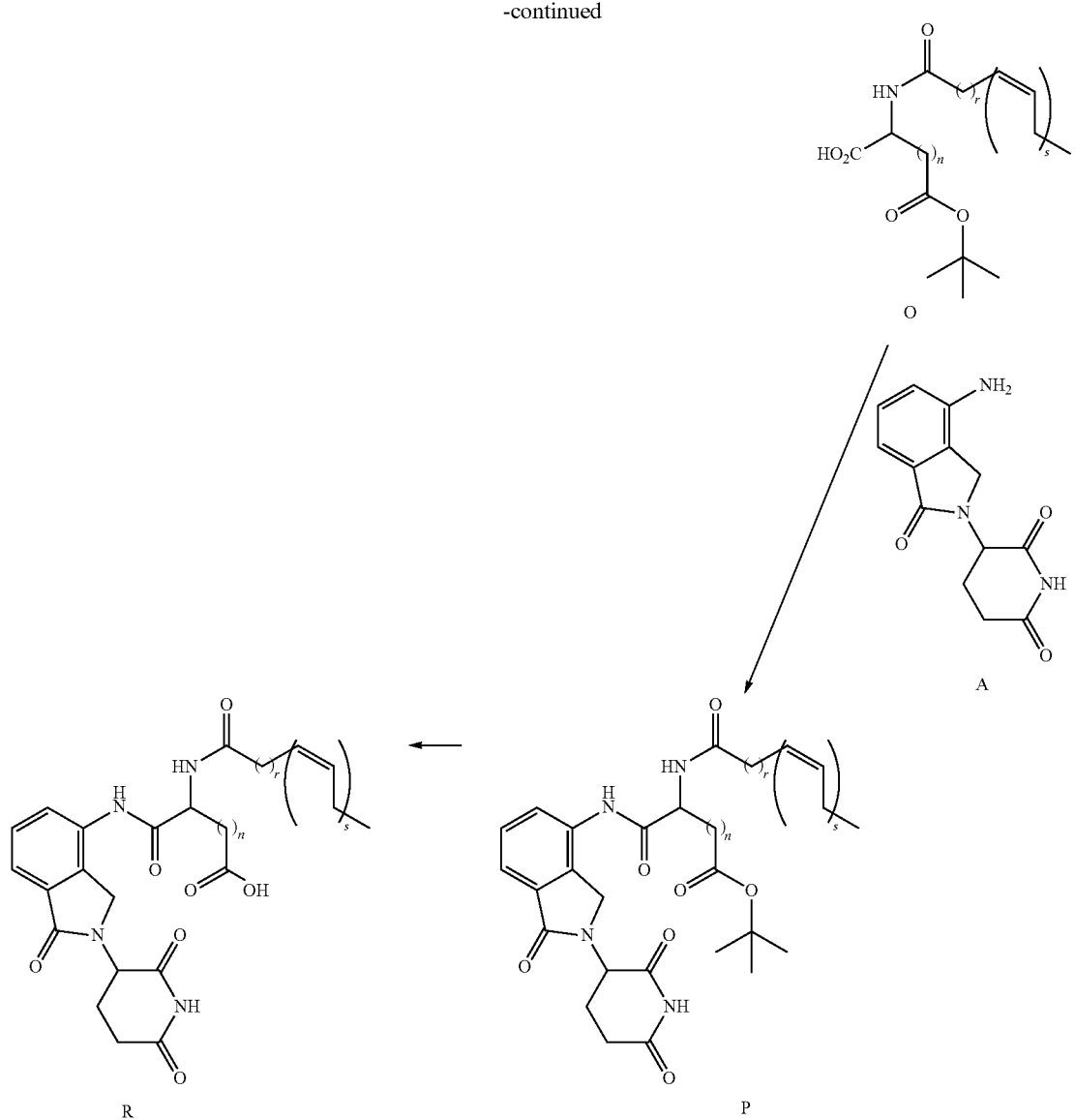

The commercially available amine M (n=1=aspartic acid; n=2=glutamic acid) is coupled with a fatty acid of the formula D using HATU/DIEA in acetonitrile to afford compounds of the formula N. The methyl ester group in compound N can be hydrolyzed to the corresponding acid by treatment with aqueous NaOH in THF or MeOH. The resulting acid O is then coupled with lenalidomide (compound A) to afford compounds of the formula P. The t-butyl group in compound P can be hydrolyzed to the corresponding acid shown in formula R by treatment with acids such as TFA in dichloromethane or HCl in dioxane.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1

TNFα Release Assay in RAW 264.7 Macrophages

The purpose of this assay is to measure the ability of small molecules to inhibit the secretion of TNFα in cultured macrophages stimulated with lipopolysaccharide (LPS). Treatment of macrophages with LPS activates inflammatory cytokine pathways primarily through the TLR4-NF-κB signaling axis. Fatty Acid Lenalidomide Derivatives inhibit the transcriptional activation of NF-κB and thus decrease the production and release of TNFα. Dexamethasone, a potent agonist of the glucocorticoid receptor is used a positive control for inhibition of TNFα release.

Day 1: Seed RAW 264.7 macrophages into 96 well culture plates. Remove culture media from RAW 264.7 cell growing in a 75 mm² tissue culture flask (cells should be at ~70% confluence) and add 10 ml of warmed complete growth media (DMEM+10% FBS+1× pen/step). The cells are scraped into suspension using a sterile plate scraper and homogenized by pipetting up and down with a 10 ml serological pipette. The cell concentration is determined using a clinical hematoctyometer. Cells are then diluted to 150,000 cells per ml into growth media. The diluted cells are then transferred to a sterile reagent reservoir and 100 µl of cell suspension is pipetted into each well of a 96 well culture plate using a multichannel pipette (15,000 cells/well). Plates are then incubated at 37° C. under normal tissue culture growth conditions (37° C., humidified $CO_2$ chamber).

Day 2: The test compound sample plate is prepared. Test compounds are prepared in growth media. Compounds are delivered to media from 1000× stocks in 100% DMSO (e.g. for a 10 µM final concentration of test compound, deliver 2 µL of 10 mM test compound to 2 ml of media). At least 150 µL of 1× compound in media is added to 96 well sample plate. Note: the perimeter wells of the 96 well plate are not used to avoid edge effects. Twelve sample wells are prepared with media plus 0.1% DMSO (these samples will serve as the vehicle controls; LPS-stimulated and non-stimulated. 10 µM dexamethasone is used as a positive control). Culture plates are then returned to the growth incubator for 2 hours. Cells are stimulated afterwards by adding 25 µl of 50 ng/ml LPS is added to every well (except the 6 unstimulated vehicle control wells: final concentration of 10 ng/mL LPS. Plates are returned to growth incubator for 3 hours. Afterwards, 100 µL of media supernatant is removed and transferred to a 96 well v-bottom sample plate. The media supernatant plate is centrifuged for 5 minutes at 1000 rpm in a swing-bucket centrifuge, pelleting any cellular debris that may remain in supernatant. 80 µL of supernatant is removed from sample plate and transferred to a fresh v-bottom 96 well plate. Cell viability is measured using Celltiter-glo kit. By measuring cell viability, a given compound's effects on TNFα secretion can show whether such effects are due to cytotoxicity or to inhibition of inflammatory signaling. 100 µL of Celltiter-glo reagent are added to each well of the cell culture plate and afterwards measure the luminescence signal (CPS) of the plate is measured using the Victor 5 plate reader (0.3 second read; 60 second plate shaking prior to read). Cell viability of a given compound at a given concentration is computed as follows:

Cell viability=CPS Sample/(Average CPS unstimulated controls)*100 Mouse TNFα ELISA Place 20 µL of media supernatant in each well for TNFα ELISA. Follow Invitrogen/Biosource manufacture's protocol for the mouse TNFα ELISA. Chromogen development is typically conducted for 20-30 minutes as described in the manufacturer's protocol. After addition of stop solution, OD 450 nm is measured using the Victor 5 plate reader (0.1 second/well scan). The TNFα secretion percent of control is then determined by using the formula:

100×(OD 450 nm Sample $X$)−(Average OD 450 nm unstimulated vehicle controls) (Average OD 450 nm LPS stimulated vehicle controls)−(Average OD 450 nm unstimulated vehicle controls)

For each test compound, TNFα secretion percent of control is plotted as a function of compound concentration using a four parameter dose-response curve fit equation (XLFIT Model #205):

$$fit=(A+((B-A)/(1+((C/x)\hat{} D))))$$

$$inv=(C/((((B-A)/(y-A))-1)\hat{}(1/D)))$$

$$res=(y-fit)$$

Example 2

Effects of the Fatty Acid Lenalidomide Conjugates on NFκB Levels in RAW 264.7 Macrophages RAW 264.7 cells transfected with an NFκB-driven luciferase reporter are plated in 96 well plates. Cells are treated with Vehicle (0.1% ethanol) or test compounds for 2 hours. As a positive control for inhibition of NF-κB signaling, 6 wells are treated with 10 µM dexamethasone. Cells are then challenged with 200 ng/mL LPS for 3 hours in the presence of test compounds. A subset of wells treated with vehicle should remain unstimulated with LPS to determine the floor signal of the assay. NF-κB driven luciferase activity is developed by addition of BriteLite luciferase kit (Perkin-Elmer) and measured using a Victor V plate reader. NF-κB activity (luciferase activity) for each treatment was normalized to Vehicle wells treated with LPS (% NFκB Response). AlamarBlue was used to monitor cell viability to ensure that inhibition of luciferase signal was not a result of compound cytotoxicity.

Example 3

In Vivo Effects of Compounds of the Invention in an LPS-Challenge TNFα Mouse Model To measure the effects of compounds on TNFα secretion in vivo, Male Swiss Webster mice (n=10 animals per group) are dosed by oral gavage with each test compound. All compounds are formulated in an aqueous solution of 0.5% carboxymethylcellulose and 0.05% TWEEN-80 (Vehicle). One hour after compound dosing, animals are treated with 0.2 mg/kg LPS (lipopolysaccharide) by intraperitoneal (IP) injection. Ninety minutes after LPS challenge, mice are anesthetized and bled by cardiac puncture into serum separator tubes (with sodium heparin). Bleeds are allowed to clot at room temperature for 2 hours, and tubes are then spun for 20 minutes at 2,000×g. Serum is harvested from tubes (100-150 µl per animal) and frozen at −70° C. TNFα serum levels are measured using commercially available TNFα ELISA kits (*$p<0.05$ using a 2-tailed t-test).

Compounds

The following non-limiting compound examples serve to illustrate further embodiments of the fatty acid lenalidomide derivatives. It is to be understood that any embodiments listed in the Examples section are embodiments of the fatty acid lenalidomide derivatives and, as such, are suitable for use in the methods and compositions described above.

Example 4

Preparation of (4Z,7Z,10Z,13Z,16Z,19Z)-N-(2-(2,6-dioxopiperidin-3-yl)-1-oxoisoindolin-4-yl)docosa-4,7,10,13,16,19-hexaenamide (I-1)

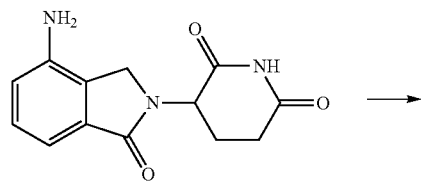

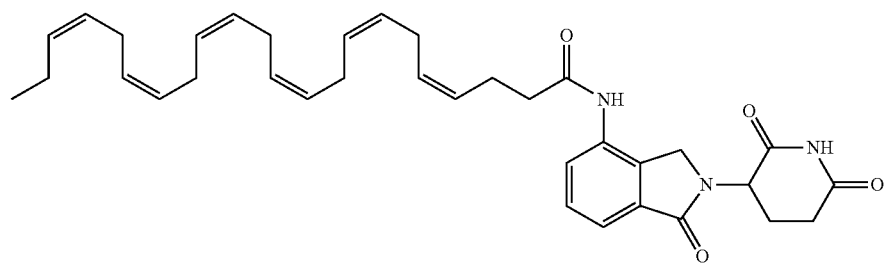 [SMILES: CC/C=C\C/C=C\C/C=C\C/C=C\C/C=C\C/C=C\CCC(=O)Nc1cccc2c1C(=O)N(C1CCC(=O)NC1=O)C2=O]

Lenalidomide (200 mg, 0.771 mmol) was taken up in 5 mL of CH$_3$CN and 2 mL of DMF along with (4Z,7Z,10Z,13Z,16Z,19Z)-docosa-4,7,10,13,16,19-hexaenoic acid (DHA, 253 mg, 0.771 mmol), HATU (322 mg, 0.848 mmol) and DIEA (200 µL, 2.3 mmol). The resulting reaction mixture was stirred at room temperature for 3 h and diluted with EtOAc (20 mL). The organic layer was washed with water (3×5 mL), brine, dried (Na$_2$SO$_4$) and concentrated under reduced pressure. Purification by silica gel chromatography (95% CH$_2$Cl$_2$, 5% MeOH) afforded 280 mg of (4Z,7Z,10Z,13Z,16Z,19Z)-N-(2-(2,6-dioxopiperidin-3-yl)-1-oxoisoindolin-4-yl)docosa-4,7,10,13,16,19-hexaenamide (63%). MS (EI) calculated for C$_{35}$H$_{43}$N$_3$O$_4$: 569.33; found: [M+H]$^+$ 570.

Example 5

Preparation of (4Z,7Z,10Z,13Z,16Z,19Z)-N-(3-((2-(2,6-dioxopiperidin-3-yl)-1-oxoisoindolin-4-yl)amino)-3-oxopropyl)docosa-4,7,10,13,16,19-hexaenamide

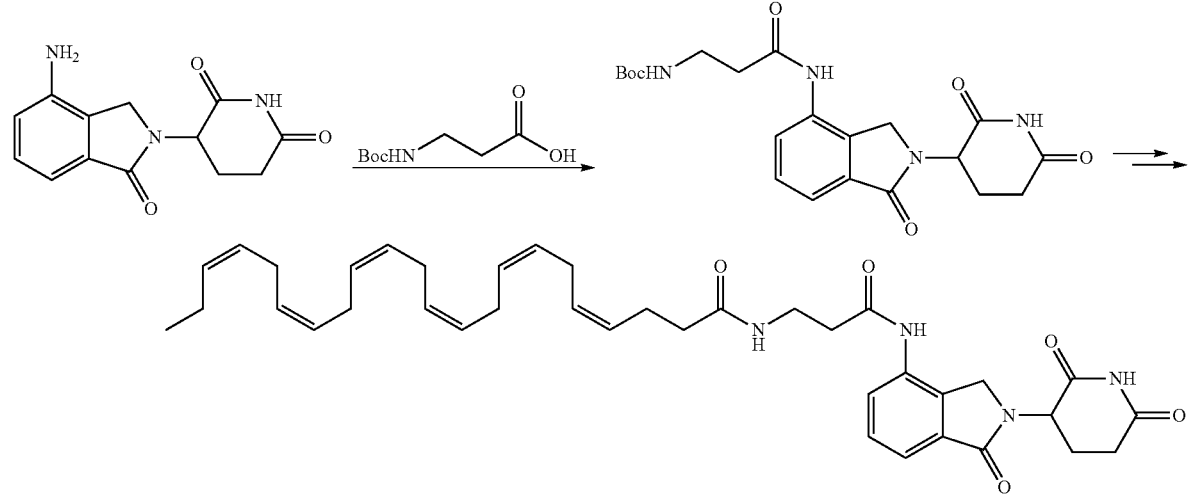

Lenolidomide (0.5 mmol) is taken up in 5 mL of acetonitrile and 2 mL of DMF along with 3-((tert-butoxycarbonyl)amino)propanoic acid (0.5 mmol), HATU (0.55 mmol) and stirred at room temperature for 18 h. The reaction mixture is concentrated under reduced pressure and then diluted with EtOAC (20 mL). The organic layer is washed with water (4×5 mL), brine (20 mL), dried ($Na_2SO_4$) and concentrated under reduced pressure. Purification by silica gel chromatography (95% $CH_2Cl_2$, 5% MeOH) affords tert-butyl (3-((2-(2,6-dioxopiperidin-3-yl)-1-oxoisoindolin-4-yl)amino)-3-oxopropyl)carbamate. This material is then taken up in 10 mL of 4 N HCl in dioxane and allowed to stir at room temperature for 6 h. The reaction mixture is then concentrated under reduced pressure to afford the HCl salt of 3-amino-N-(2-(2,6-dioxopiperidin-3-yl)-1-oxoisoindolin-4-yl)propanamide.

The HCl salt of 3-amino-N-(2-(2,6-dioxopiperidin-3-yl)-1-oxoisoindolin-4-yl)propanamide (0.1 mmol) is taken up in 5 mL of DMF along with (4Z,7Z,10Z,13Z,16Z,19Z)-docosa-4,7,10,13,16,19-hexaenoic acid (DHA, 0.1 mmol), HATU (0.11 mmol) and DIEA (0.3 mmol). The resulting reaction mixture is stirred at room temperature for 4 h and then diluted with EtOAc (20 mL). The organic layer is washed with water (3×5 mL), brine (20 mL), dried ($Na_2SO_4$) and concentrated under reduced pressure. Purification by silica gel chromatography (95% $CH_2Cl_2$, 5% MeOH) affords (4Z,7Z,10Z,13Z,16Z,19Z)-N-(3-((2-(2,6-dioxopiperidin-3-yl)-1-oxoisoindolin-4-yl)amino)-3-oxopropyl)docosa-4,7,10,13,16,19-hexaenamide.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A compound of Formula I:

or a pharmaceutically acceptable salt, hydrate, solvate, enantiomer or stereoisomer thereof; wherein $W_1$ and $W_2$ are each independently null, O, S, NH, NR, or $W_1$ and $W_2$ can be taken together can form an imidazolidine or piperazine group;

each a, b, c, and d is independently —H, -D, —$CH_3$, —$OCH_3$, —$OCH_2CH_3$, —C(O)OR, —O-Z, or benzyl, or two of a, b, c, and d can be taken together, along with the single carbon to which they are bound, to form a cycloalkyl or heterocycle;

each n, o, p, and q is independently 0, 1, or 2;

each u is independently 0 or 1;

L is independently null, —O—, —S—, —S(O)—, —S($O)_2$—, —S—S—, —($C_1$-$C_6$alkyl)—, —($C_3$-$C_6$ cycloalkyl)-, a heterocycle, a heteroaryl,

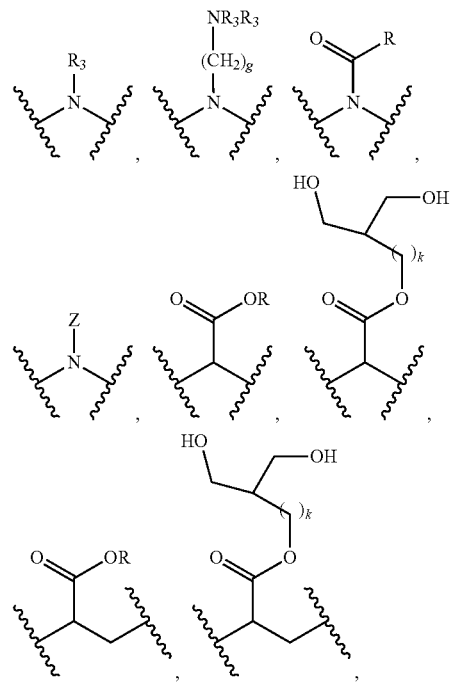

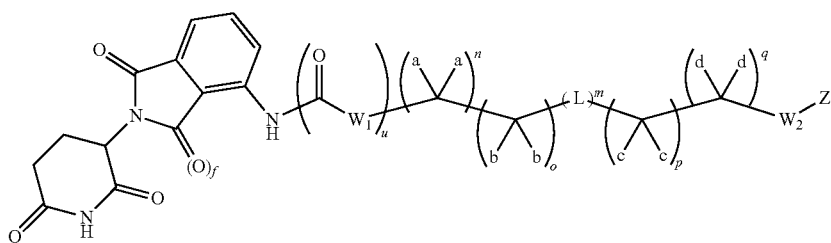

Formula I

-continued

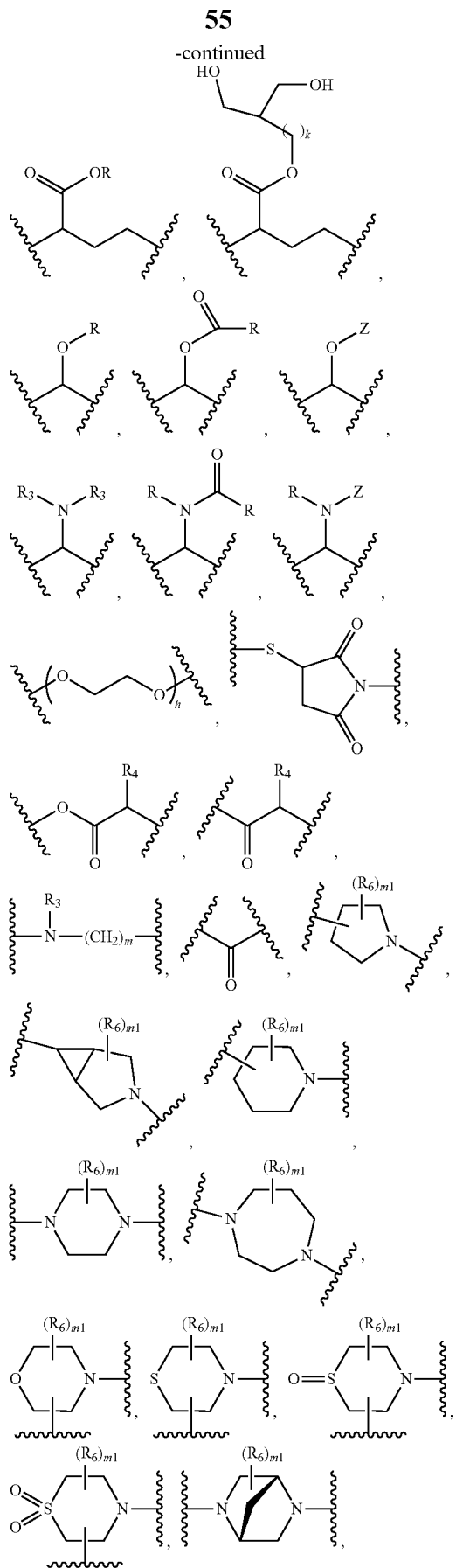

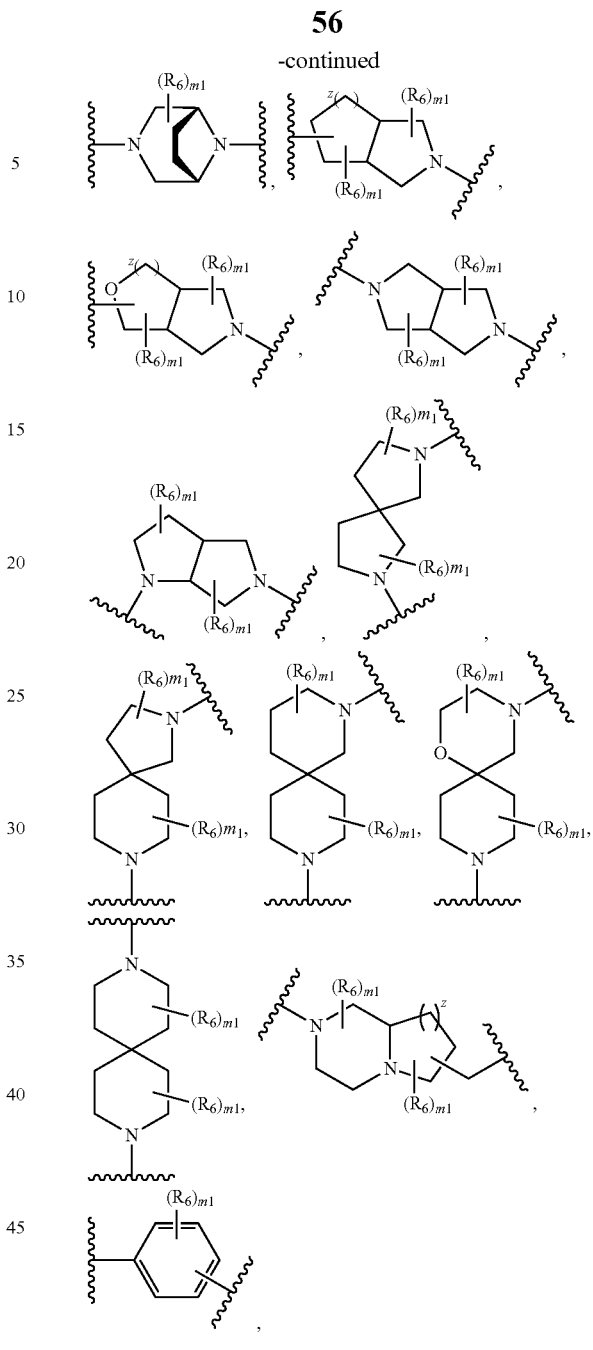

wherein the representation of L is not limited directionally left to right as is depicted, rather either the left side or the right side of L can be bound to the $W_1$ side of the compound of Formula I;

$R_6$ is independently —H, -D, —$C_1$-$C_4$ alkyl, -halogen, cyano, oxo, thiooxo, —OH, —C(O)$C_1$-$C_4$ alkyl, —O-aryl, —O-benzyl, —OC(O)$C_1$-$C_4$ alkyl, —$C_2$-$C_3$ alkene, —$C_2$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;

each f is independently 0 or 1;
each g is independently 2, 3 or 4;
each h is independently 1, 2, 3 or 4;
m is 0, 1, 2, 3, 4 or 5; if m is more than 1, then L can be the same or different;

m1 is 0, 1, 2 or 3;

k is 0, 1, 2, or 3;

z is 1, 2, or 3;

each $R_3$ is independently H or $C_1$-$C_6$ alkyl that can be optionally substituted with either O or N and in $NR_3R_3$, both $R_3$ when taken together with the nitrogen to which they are attached can form a heterocyclic ring such as a pyrrolidine, piperidine, morpholine, piperazine or pyrrole;

each $R_4$ independently e, H or straight or branched $C_1$-$C_{10}$ alkyl which can be optionally substituted with OH, $NH_2$, $CO_2R$, $CONH_2$, phenyl, $C_6H_4OH$, imidazole or arginine;

each e is independently H or any one of the side chains of the naturally occurring amino acids;

each Z is independently —H,

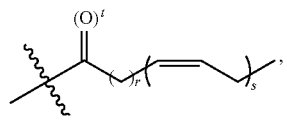

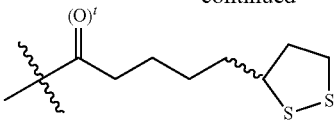

in the compound;

each r is independently 2, 3, or 7;

each s is independently 3, 5, or 6;

each t is independently 0 or 1;

each v is independently 1, 2, or 6;

$R_1$ and $R_2$ are independently —H, -D, —$C_1$-$C_4$ alkyl, -halogen, —OH, —C(O)$C_1$-$C_4$ alkyl, -O-aryl, —O-benzyl, —OC(O)$C_1$-$C_4$ alkyl, —$C_2$-$C_3$ alkene, —$C_2$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2C_1$-$C_3$ alkyl; and each R is independently —H, —$C_1$-$C_3$ alkyl, or straight or branched $C_1$-$C_4$ alkyl optionally substituted with OH, or halogen.

2. A compound of the Formula Ia:

Formula Ia

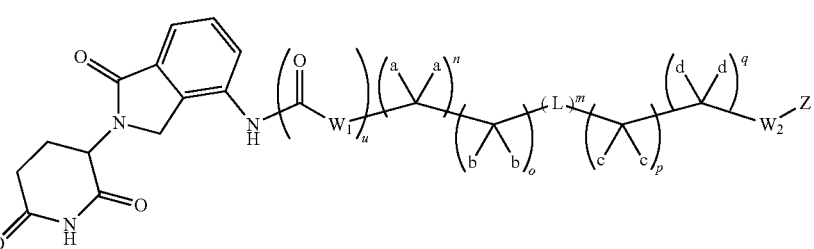

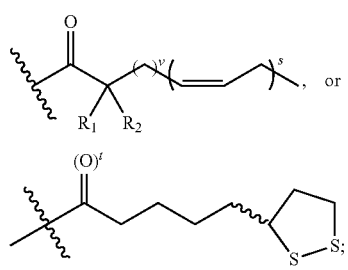

-continued

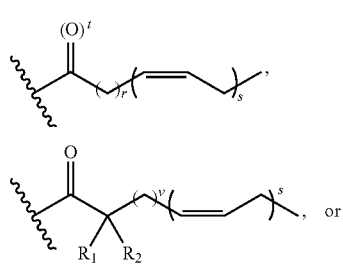

with the proviso that there is at least one of or a pharmaceutically acceptable salt, hydrate, solvate, enantiomer or stereoisomer thereof; wherein $W_1$ and $W_2$ are each independently null, O, S, NH, NR, or $W_1$ and $W_2$ can be taken together can form an imidazolidine or piperazine group;

each a, b, c, and d is independently —H, -D, —$CH_3$, —$OCH_3$, —$OCH_2CH_3$, —C(O)OR, —O-Z, or benzyl, or two of a, b, c, and d can be taken together, along with the single carbon to which they are bound, to form a cycloalkyl or heterocycle;

each n, o, p, and q is independently 0, 1, or 2;

each u is independently 0 or 1;

L is independently null, —O—, —S—, —S(O)—, —S(O)$_2$, —S—S—, ($C_1$-$C_6$alkyl)-, —($C_3$-$C_6$cycloalkyl)-, a heterocycle, a heteroaryl,

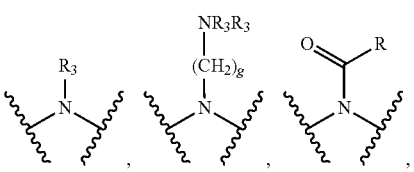

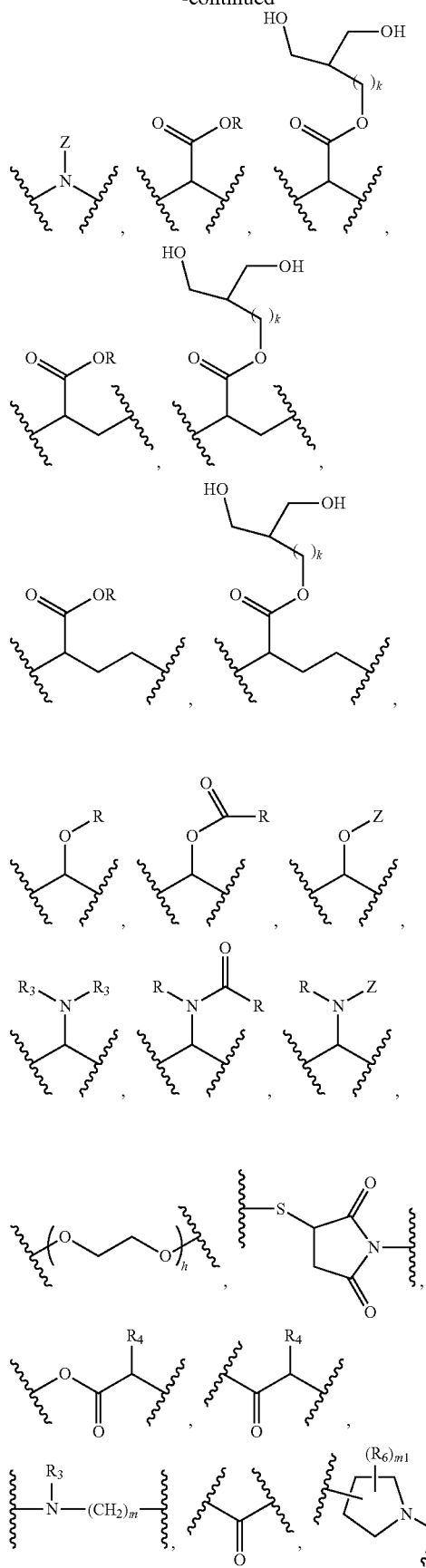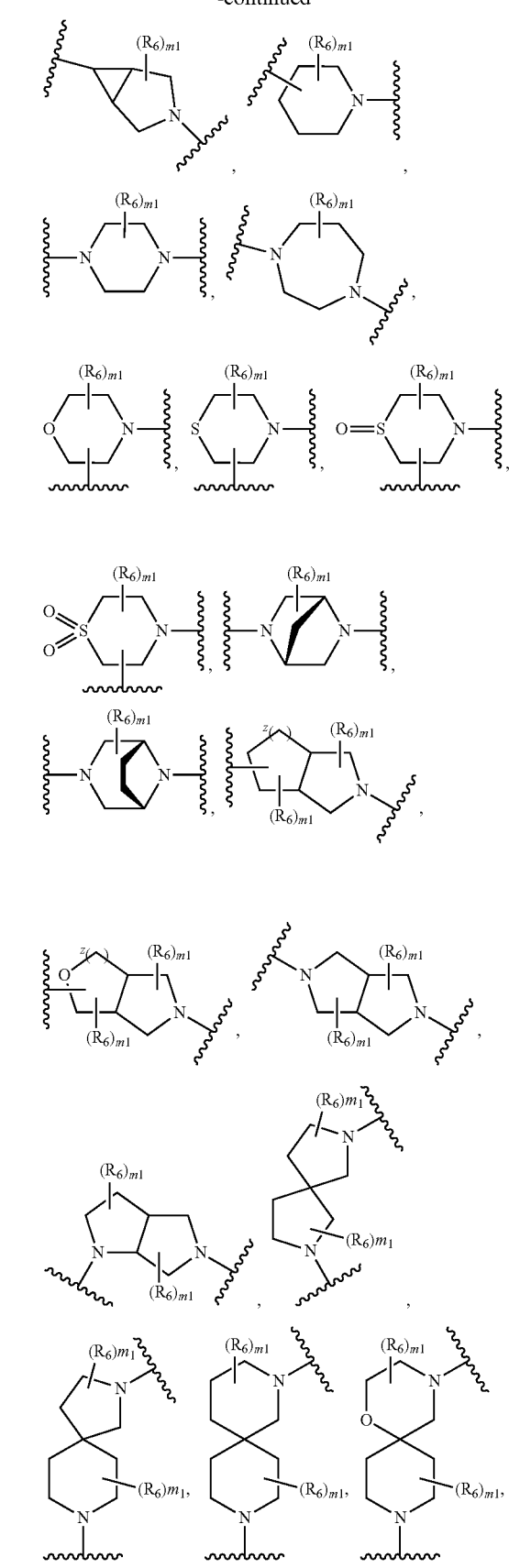

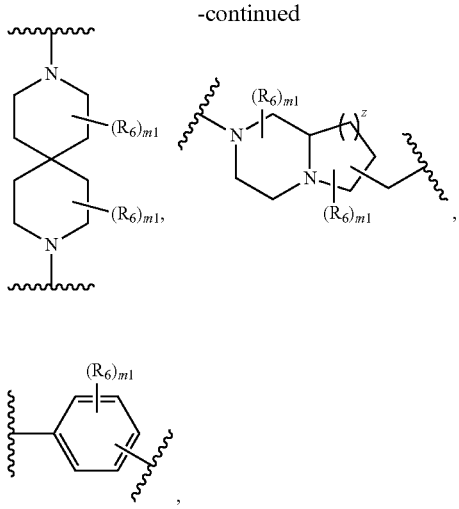

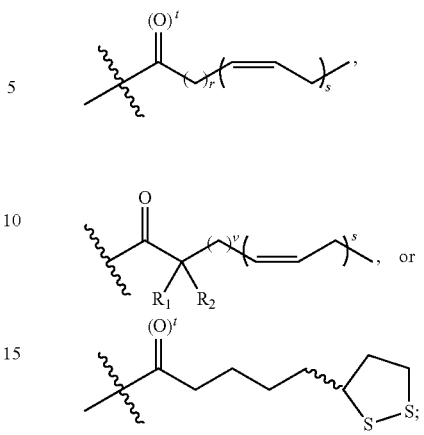

wherein the representation of L is not limited directionally left to right as is depicted, rather either the left side or the right side of L can be bound to the $W_1$ side of the compound of Formula Ia;

$R_6$ is independently —H, -D, —$C_1$-$C_4$ alkyl, -halogen, cyano, oxo, thiooxo, —OH, —C(O)$C_1$-$C_4$ alkyl, —O-aryl, —O-benzyl, —OC(O)$C_1$-$C_4$ alkyl, —$C_2$-$C_3$ alkene, —$C_2$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;

each g is independently 2, 3 or 4;

each h is independently 1, 2, 3 or 4;

m is 0, 1, 2, 3, 4 or 5; if m is more than 1, then L can be the same or different;

m1 is 0, 1, 2 or 3;

k is 0, 1, 2, or 3;

z is 1, 2, or 3;

each $R_3$ is independently H or $C_1$-$C_6$ alkyl that can be optionally substituted with either 0 or N and in $NR_3R_3$, both $R_3$ when taken together with the nitrogen to which they are attached can form a heterocyclic ring such as a pyrrolidine, piperidine, morpholine, piperazine or pyrrole;

each $R_4$ independently e, H or straight or branched $C_1$-$C_{10}$ alkyl which can be optionally substituted with OH, $NH_2$, $CO_2R$, $CONH_2$, phenyl, $C_6H_4OH$, imidazole or arginine;

each e is independently H or any one of the side chains of the naturally occurring amino acids;

each Z is independently —H, with the proviso that there is at least one of

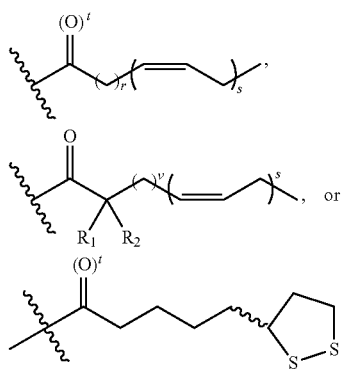

in the compound;

each r is independently 2, 3, or 7;

each s is independently 3, 5, or 6;

each t is independently 0 or 1;

each v is independently 1, 2, or 6;

$R_1$ and $R_2$ are independently —H, -D, —$C_1$-$C_4$ alkyl, -halogen, —OH, —C(O)$C_1$-$C_4$ alkyl, —O-aryl, —O-benzyl, —OC(O)$C_1$-$C_4$ alkyl, —$C_2$-$C_3$ alkene, —$C_2$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl; and each R is independently —H, —$C_1$-$C_3$ alkyl, or straight or branched $C_1$-$C_4$ alkyl optionally substituted with OH, or halogen.

3. The compound of claim 2 selected from the group consisting of

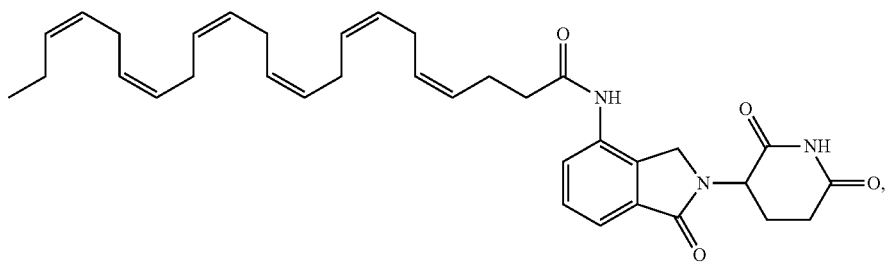 [SMILES: CC/C=C\C/C=C\C/C=C\C/C=C\C/C=C\C/C=C\CCC(=O)Nc1cccc2c1CN(C1CCC(=O)NC1=O)C2=O]

(4Z,7Z,10Z,13Z,16Z,19Z)-N-(2-(2,6-dioxopiperidin-3-yl)-1-oxoisoindolin-4-yl)docosa-4,7,10,13,16,19-hexaenamide (I-1);

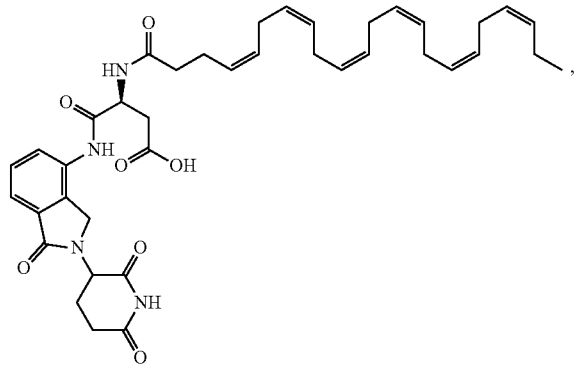 [SMILES: CC/C=C\C/C=C\C/C=C\C/C=C\C/C=C\C/C=C\CCC(=O)N[C@@H](CC(=O)O)C(=O)Nc1cccc2c1CN(C1CCC(=O)NC1=O)C2=O]

(S)-4-(2-(2,6-dioxopiperidin-3-yl)-1-oxoisoindolin-4-ylamino)-3-((4Z,7Z,10Z,13Z,16Z,19Z)-docosa-4,7,10,13,16,19-hexaenamido)-4-oxobutanoic acid (I-3):

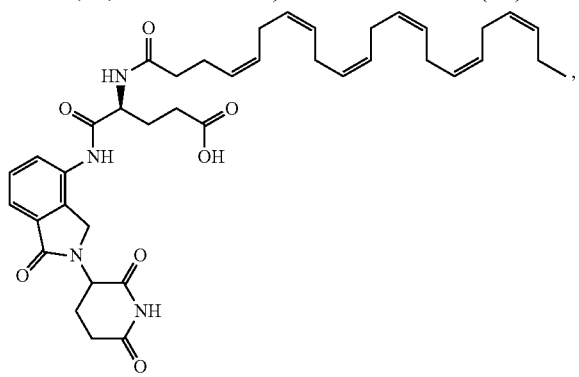

(S)-5-(2-(2,6-dioxopiperidin-3-yl)-1-oxoisoindolin-4-ylamino)-4-((4Z,7Z,10Z,13Z,16Z,19Z)-docosa-4,7,10,13,16,19-hexaenamido)-5-oxopentanoic acid (I-4);

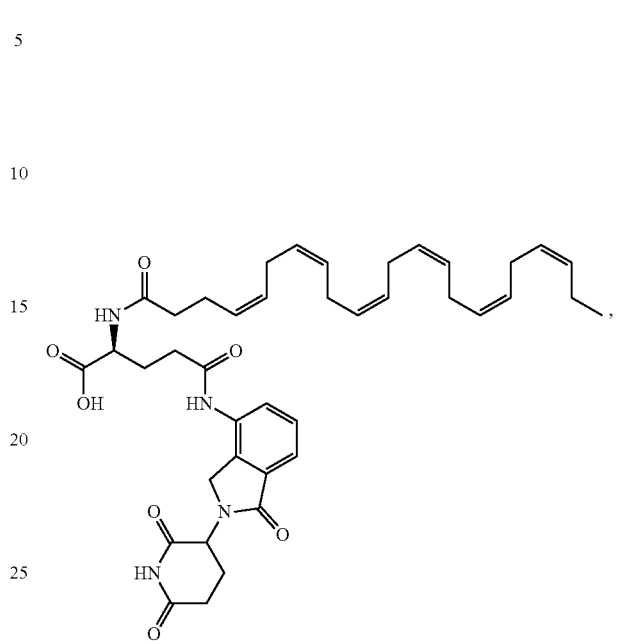

(S)-5-(2-(2,6-dioxopiperidin-3-yl)-1-oxoisoindolin-4-ylamino)-2-((4Z,7Z,10Z,13Z,16Z,19Z)-docosa-4,7,10,13,16,19-hexaenamido)-5-oxopentanoic acid (I-5); and

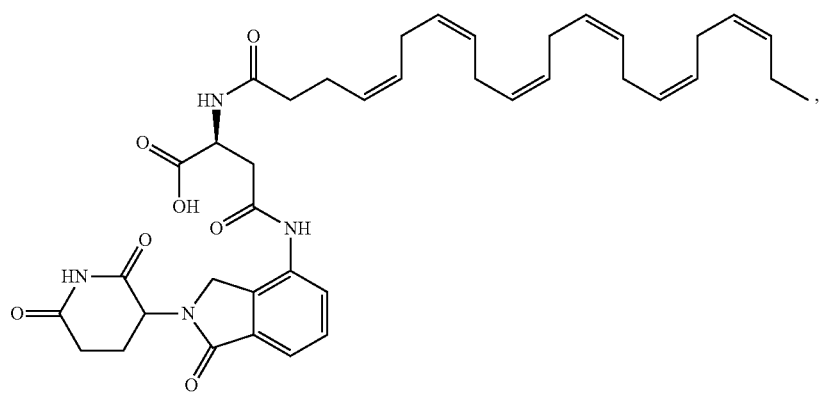 [SMILES: CC/C=C\C/C=C\C/C=C\C/C=C\C/C=C\C/C=C\CCC(=O)N[C@@H](CC(=O)Nc1cccc2c1CN(C1CCC(=O)NC1=O)C2=O)C(=O)O]

(S)-2-((4Z,7Z,10Z,13Z,16Z,19Z)-docosa-4,7,10,13,16,19-hexaenamido)-4-((3-hydroxy-5-(hydroxymethyl)-2-methylpyridin-4-yl)methylamino)-4-oxobutanoic acid (I-6).

4. A pharmaceutical composition comprising a compound of or 1 and a pharmaceutically acceptable carrier.

5. A pharmaceutical composition comprising a compound of claim 2 and a pharmaceutically acceptable carrier.

6. A pharmaceutical composition comprising a compound of claim 3 and a pharmaceutically acceptable carrier.

* * * * *

UNITED STATES PATENT AND TRADEMARK OFFICE
CERTIFICATE OF CORRECTION

Page 1 of 1

PATENT NO. : 9,029,548 B2
APPLICATION NO. : 13/464435
DATED : May 12, 2015
INVENTOR(S) : Jill C. Milne et al.

It is certified that error appears in the above-identified patent and that said Letters Patent is hereby corrected as shown below:

In the claims,

In claim 1 at column 57, line 10, replace "each $R_4$ independently" with -- each $R_4$ is independently --.

In claim 2 at column 61, line 42, replace "either 0 or N" with -- either O or N --.

In claim 4 at column 64, line 60, replace "of or 1" with -- of claim 1 --.

Signed and Sealed this
First Day of December, 2015

Michelle K. Lee
*Director of the United States Patent and Trademark Office*